US009737644B2

(12) United States Patent
Pulapura et al.

(10) Patent No.: US 9,737,644 B2
(45) Date of Patent: *Aug. 22, 2017

(54) MEDICAL DEVICE COATINGS

(71) Applicant: TYRX, Inc., Monmouth Junction, NJ (US)

(72) Inventors: Satish Pulapura, Bridgewater, NJ (US); Qing Ge, Solon, OH (US)

(73) Assignee: TYRX, Inc., Monmouth Junction, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/861,597

(22) Filed: Sep. 22, 2015

(65) Prior Publication Data

US 2016/0008521 A1   Jan. 14, 2016

Related U.S. Application Data

(63) Continuation of application No. 13/218,096, filed on Aug. 25, 2011, now Pat. No. 9,155,735.

(60) Provisional application No. 61/376,790, filed on Aug. 25, 2010.

(51) Int. Cl.
| | | |
|---|---|---|
| *A61F 2/00* | (2006.01) | |
| *C08G 69/08* | (2006.01) | |
| *A61L 31/10* | (2006.01) | |
| *A61K 31/155* | (2006.01) | |
| *A61K 31/496* | (2006.01) | |
| *A61K 31/65* | (2006.01) | |
| *A61K 33/38* | (2006.01) | |
| *C09D 5/14* | (2006.01) | |
| *C09D 171/02* | (2006.01) | |
| *A61L 31/16* | (2006.01) | |

(52) U.S. Cl.
CPC ............ *A61L 31/10* (2013.01); *A61K 31/155* (2013.01); *A61K 31/496* (2013.01); *A61K 31/65* (2013.01); *A61K 33/38* (2013.01); *A61L 31/16* (2013.01); *C09D 5/14* (2013.01); *C09D 171/02* (2013.01); *A61L 2300/204* (2013.01); *A61L 2300/216* (2013.01); *A61L 2300/404* (2013.01); *A61L 2300/606* (2013.01); *A61L 2420/06* (2013.01); *Y10T 428/265* (2015.01); *Y10T 428/31678* (2015.04)

(58) Field of Classification Search
None
See application file for complete search history.

(56) References Cited

U.S. PATENT DOCUMENTS

| | | |
|---|---|---|
| 4,298,997 A | 11/1981 | Rybka |
| 4,326,532 A | 4/1982 | Hammar |
| 5,216,115 A | 6/1993 | Kohn et al. |
| 5,217,493 A | 6/1993 | Raad et al. |
| 5,614,284 A | 3/1997 | Kranzler et al. |
| 5,676,146 A | 10/1997 | Scarborough |
| 6,120,491 A | 9/2000 | Kohn et al. |
| 6,548,569 B1 | 4/2003 | Williams et al. |
| 6,656,488 B2 | 12/2003 | Yi et al. |
| 6,838,493 B2 | 1/2005 | Williams et al. |
| 6,887,270 B2 | 5/2005 | Miller et al. |
| 6,981,944 B2 | 1/2006 | Jamiolkowski et al. |
| 8,315,700 B2 | 11/2012 | Citron et al. |
| 2002/0072694 A1 | 6/2002 | Snitkin et al. |
| 2003/0091609 A1 | 5/2003 | Hendriks |
| 2003/0153983 A1 | 8/2003 | Miller et al. |
| 2004/0147688 A1 | 7/2004 | Kemnitzer et al. |
| 2004/0172048 A1 | 9/2004 | Browning |
| 2004/0186529 A1 | 9/2004 | Bardy et al. |
| 2004/0209538 A1 | 10/2004 | Klinge et al. |
| 2005/0008671 A1 | 1/2005 | Van Antwerp |
| 2005/0052466 A1 | 3/2005 | Frazer et al. |
| 2005/0101692 A1 | 5/2005 | Sohier et al. |
| 2005/0118227 A1 | 6/2005 | Kohn et al. |
| 2005/0143817 A1 | 6/2005 | Hunter et al. |
| 2005/0147690 A1 | 7/2005 | Masters et al. |
| 2005/0149157 A1 | 7/2005 | Hunter et al. |
| 2005/0161859 A1 | 7/2005 | Miller et al. |
| 2005/0163821 A1 | 7/2005 | Sung et al. |
| 2005/0177225 A1 | 8/2005 | Hunter et al. |
| 2005/0208664 A1 | 9/2005 | Keegan et al. |
| 2005/0209664 A1 | 9/2005 | Hunter et al. |
| 2005/0228471 A1 | 10/2005 | Williams et al. |
| 2006/0025852 A1 | 2/2006 | Armstrong et al. |
| 2006/0034769 A1 | 2/2006 | Kohn et al. |
| 2006/0052466 A1 | 3/2006 | Handa |
| 2006/0147492 A1 | 7/2006 | Hunter et al. |
| 2006/0246103 A1 | 11/2006 | Ralph et al. |
| 2007/0198040 A1 | 8/2007 | Buevich et al. |

(Continued)

FOREIGN PATENT DOCUMENTS

| | | |
|---|---|---|
| WO | 9924107 A1 | 5/1999 |
| WO | 2008137807 A1 | 11/2008 |
| WO | 2010006046 A1 | 1/2010 |
| WO | 2010141475 A1 | 12/2010 |

OTHER PUBLICATIONS

International Search Report and Written Opinion for Application No. PCT/US2011/049140 dated Aug. 27, 2012.

*Primary Examiner* — Susannah Chung
*Assistant Examiner* — Robert T Butcher
(74) *Attorney, Agent, or Firm* — Sorell Lenna & Schimdt, LLP

(57) ABSTRACT

The present invention relates to coatings comprising polyethylene glycol and at least one polyphenolic polymer. In particular, the polyphenolic polymer could be selected from the group consisting of tyrosine-derived polyarylates, linear polyesteramides, dihydroxybenzoate polymers, and resorcinol-derived polymers. The coating of the present invention may also include a drug, such as an antibiotic. The coatings of the present invention are suitable for use as coatings for medical devices, such as orthopedic pins or stents.

19 Claims, 21 Drawing Sheets

(56) References Cited

U.S. PATENT DOCUMENTS

| | | |
|---|---|---|
| 2007/0213416 A1 | 9/2007 | Handa et al. |
| 2009/0149568 A1 | 6/2009 | Pacetti |
| 2010/0074940 A1 | 3/2010 | Schwartz et al. |
| 2010/0112087 A1* | 5/2010 | Harrison .............. A61K 9/7007 424/615 |

* cited by examiner

The effect of sterilization on the molecular weight and drug content of the coating.

Cumulative release of minocycline and rifampin from the coated pins as a function of time Zone of Inhibition (ZOI) for various coated substrates Stickiness of substrates coated with P22-27.5% Blends of PEGS Stickiness' of substrates coated with P64 blended with 10% of PEG-400, PEG-Acid, PEG-1000, or PEG-3350 as compared to Teflon Stickiness' of substrates coated with P64 blended with 10% of PEG-400, PEG-Acid, PEG-1000, or PEG-3350 as compared to Teflon Stickiness of substrates coated with P(DTPP Glutarate), P(MeDHB-15 DHB Glutarate), or P(TE-DG-TE-Glutarate) - Blends with various PEGs S. aureus-infected post-operative knee joint Uninfected post-operative knee joint

MEDICAL DEVICE COATINGS

CROSS-REFERENCE TO RELATED APPLICATIONS

This application is a continuation of U.S. patent application Ser. No. 13/218,096, filed Aug. 25, 2011, which claims the benefit of U.S. Provisional Patent Application No. 61/376,790, filed Aug. 25, 2010. These applications are hereby incorporated by reference herein in their entireties.

BACKGROUND

The incidence of infections after total joint replacement surgery has increased over the past decade despite the widespread use of intravenous antibiotic prophylaxis and a focus on aseptic surgical technique. Post-arthroplasty infections still occur in about 1.2% of primary arthroplasties and 3-5% of revisions. As the demand for joint replacements increases with the aging population, the total number of infections is projected to rise from 17,000 to 266,000 per year by 2030 as the number of arthroplasties exceeds 3.8 million surgeries. The treatment of a post-arthroplasty infection is exceedingly difficult. Bacteria (especially *S. aureus*) form extracellular anionic polysaccharide biofilms on implanted metallic/plastic materials that block penetration of immune cells and antibiotics, promoting bacterial survival. Once a biofilm is formed, surgical removal of all the implanted materials is necessary. Most of these infections are caused by staphylococcal species (about 70%) and an increasing number are due to virulent antibiotic-resistant strains such as methicillin-resistant *S. aureus* (MRSA), which further complicate treatment.

The current standard of care in the U.S. to treat a chronic post-arthroplasty infection is a two-stage procedure beginning with (1) surgical removal of all prosthetic components and bone cement, debridement of necrotic/granulation tissue, placement of an antibiotic-impregnated spacer, administration of a 6-week course of intravenous antibiotics (during which the patient is unable to bear weight on the affected limb), and (2) revision arthroplasty after the infection has cleared. In severe infections and refractory cases, arthrodesis, resection arthroplasty and amputation are sometimes necessary. In the elderly, these infections result in increased mortality. Overall, the treatment of post-arthroplasty infection involves extensive medical and surgical care, prolonged disability/rehabilitation and significantly worse outcomes. In addition, these infections represent an enormous economic burden due to additional medical costs and resource utilization as well as indirectly through lost wages and productivity. These medical costs alone average $144,514 (compared with $30,173 for an uncomplicated arthroplasty), which correspond to an annual national healthcare burden of $8.63 billion by 2015.

Most post-arthroplasty infections are thought to be caused by invading bacteria at the time of surgery. As treatment of infected implanted materials is exceedingly difficult, especially due to the inherent difficulties in treating an established biofilm, one potential therapeutic strategy is to focus on the prevention of infection.

One way to avoid infection is to use implantable devices that deliver a drug, such as an antibiotic, directly to the implantation site. Local delivery of certain drugs can be more effective than traditional systemic routs, as certain tissues, particularly bone tissue, have limited vascularity. Additionally, local delivery allows for a high local concentration while avoiding systemic side-effects.

Local delivery of a large bolus dose at the time of surgery would not provide long term effects. While pumps to deliver drugs to a local site may be used in certain cases, they are not feasible in all circumstances and can be cumbersome.

In order to achieve local, continuous delivery of a drug, medical devices can be coated with a drug in a manner that would allow the sustained and localized release of the drug.

Implantable medical devices can be made from various materials, including, but not limited to, metals, polymers or a combination of different materials. Metals commonly used in implantable medical devices include, but are not limited to, titanium and stainless steel. Common polymers, include, but are not limited to, polyethylene and polypropylene. However, due to the differences in surface energies between polymers and metals, what may be a suitable coating on one material will not be effective on another.

While metals have surface energies of around 100, the surface energy of a polymer is typically around 30. The relative surface energies of a surface and coating material affect the ability of the coating material to effectively adhere to the surface. In order for a liquid (such as a coating solution) to optimally adhere to a surface, it must thoroughly "wet out" the surface to which it is to be bonded. "Wetting out" means that the liquid flows and covers a surface to maximize the contact area and the attractive forces between the liquid and solid surface. For a liquid such as an adhesive or coating solution to effectively wet out a surface, the surface energy of the liquid must be as low as or lower than the surface energy of the substrate. Standard adhesive or coating formulations wet out and bond to high surface energy (HSE) surfaces such as metal or ABS plastic, but fail to bond to low surface energy (LSE) polyolefins that include polypropylene and polyethylene.

For traditional structural adhesives or coatings to bond low surface energy substrates such as polyolefins, surface treatments, such as exposure to UV light or treatment with chromic acid, have been used to raise the substrate surface energy by as much as 30% to better meet the adhesive surface energy. Other strategies to modify the surface properties and precisely tune interfacial interactions of materials include, lithographic patterning, binary assembly, anodic oxidation, electrodeposition and chemical etching, plasma etching, laser treating, ion bombardment, UV light inducement, surfactants, chemical oxidation treatment, polymer modification, electrospinning, electrochemical etching, chemical vapor deposition, sol-gelprocessing, and so on. Although high quality surfaces can be fabricated by the above mentioned approaches, these methods all have some disadvantages limiting their further applications, such as the complexity of experimental setup, rigorous preparation conditions, higher energy cost and the dependence on the specific surface chemistries. Moreover, these methods are only suitable for some given substrates and cannot be applied to a wide range of surfaces or substrates.

For example, current state of the art drug-eluting stents usually have one to three or more layers in the coating e.g. a base layer for adhesion, a main layer for holding the drug, and sometimes a top coat to slow down the release of the drug and extend its effect. For example, the CYPHER® stent requires an initial base-layer of parylene to allow for adhesion of the drug containing polymer. Replacing these multiple coats with a single coating would result in more straightforward manufacturing.

US Patent Application No. 2007/0198040 A1 describes a bioresorbable polymer coating on a surgical mesh as a carrier for the antimicrobial agents rifampin and minocyline. However, a coating suitable for a polypropylene mesh may not provide enough adhesion to medical devices, such as orthopedic pins, which are made of metal and/or undergo significant manipulation and abrasion during surgical installation.

Therefore, there is a need for polymeric coatings that can provide improved adhesion to substrates with varying surface properties. Furthermore, these coatings should also be biocompatible in order to avoid rejection; sturdy/sticky to avoid peeling off during implantation; biodegradable/resorbable so there is no long term foreign body response; capable of sustained delivery of drugs; easily tailored to deliver variety of drugs; easily tailored for coating onto different substrates; easily applied to a variety of devices by spraying; dipping or melting; and compatible with other excipients. It has been surprisingly discovered that a blend of certain polyphenolic polymers and polyethylene glycol does provide such properties when coated onto medical devices having a wide range of different surface characteristics.

SUMMARY OF THE INVENTION

The present invention is directed towards an improved coating for a medical device, where the coating comprises a mixture of polyethylene glycol, at least one polyphenolic polymer, and optionally at least one drug.

In some embodiments, the polyethylene glycol is selected from the group consisting of poloxamers, PEG-3350, PEG-1000, PEG-400, or PEGs having modified end caps.

In some embodiments, the polyphenolic polymer is a selected from the group consisting of tyrosine-derived polyarylates, linear polyesteramides, dihydroxybenzoate polymers, and resorcinol-derived polymers as described herein.

Suitable tyrosine-derived polyarylates include those of Formula (I):

$$\left[ -O-\phantom{}\!\!\bigcirc\!\!\phantom{}-R_1-\overset{O}{\underset{\phantom{}}{C}}-NH-CH-CH_2-\phantom{}\!\!\bigcirc\!\!\phantom{}-O-\overset{O}{\underset{\phantom{}}{C}}-R_2-\overset{O}{\underset{\phantom{}}{C}}- \right] \quad (I)$$
$$\underset{Y}{\overset{\mid}{C}=O}$$

wherein $R_1$ is independently selected from CH=CH or $(CH_2)_n$, n ranges from 0 to 18;

Y is selected from the group consisting of $C_1$-$C_{18}$ alkylamino, —OR', —NHCH$_2$CO$_2$R', —NH(CH$_2$)$_q$OR', —NH(CH$_2$CH$_2$O)$_p$R', —NH(CH$_2$CH$_2$CH$_2$O)$_p$R',

[structures showing benzoate ester, tris(hydroxymethyl) aminomethane, and amino sugar moieties]

, and ;

q ranges from 0 to 4;
p ranges from 1 to 5000;
R' is independently selected from the group consisting of H, $C_1$-$C_{18}$ alkyl, $C_2$-$C_{18}$ alkenyl, $C_8$-$C_{14}$ alkylaryl, benzyl, and substituted benzyl;

$R_2$ is independently selected from the group consisting of a divalent, linear or branched, substituted or unsubstituted alkylene, alkenylene, alkynylene, arylene, alkylarylene, alkyl ether or aryl ether moiety having from 1 to 30 carbon atoms; —(R$_5$)$_q$O((CR$_3$R$_4$)$_r$O)$_s$(R$_5$)$_q$—; and —(R$_5$)$_q$CO$_2$((CR$_3$R$_4$)$_r$O)$_s$CO(R$_5$)$_q$—;

$R_3$ and $R_4$ are independently selected from the group consisting of hydrogen and, a linear or branched, substituted or unsubstituted alkyl having from 1 to 10 carbon atoms; and $R_5$ is independently selected from the group consisting of a linear or branched, lower alkylene or lower alkenylene.

Suitable linear polyesteramides comprise one or more monomer units having the formula:

$$-O-\phantom{}\!\!\bigcirc\!\!\phantom{}^{Z_1}-R-CH-NH-\overset{O}{\underset{\phantom{}}{C}}-R_2-\overset{O}{\underset{\phantom{}}{C}}-Y$$
$$\underset{COOR_1}{\overset{\mid}{\phantom{C}}}$$

wherein R is —(CR$_3$R$_4$)$_a$ or —CR$_3$=CR$_4$—;

$R_1$ is selected from the group consisting of hydrogen, a saturated or unsaturated, substituted or unsubstituted alkyl, aryl, alkylaryl or alkyl ether having from 1 to 20 carbon atoms, and —(R$_5$)$_q$O((CR$_3$R$_4$)$_r$O)$_s$—R$_6$;

$R_2$ is selected from the group consisting of a divalent, linear or branched, substituted or unsubstituted alkylene, alkenylene, alkynylene, arylene, alkylarylene, alkyl ether or aryl ether moiety having from 1 to 30 carbon atoms; —(R$_5$)$_q$O((CR$_3$R$_4$)$_r$O)$_s$(R$_5$)$_q$—, and —(R$_5$)$_q$CO$_2$((CR$_3$R$_4$)$_r$O)$_s$CO(R$_5$)$_q$—;

$R_3$ and $R_4$ are independently selected from the group consisting of hydrogen and a linear or branched, substituted or unsubstituted alkyl having from 1 to 10 carbon atoms;

$R_5$ is independently selected from the group consisting of a linear or branched lower alkylene or lower alkenylene group;

$R_6$ is independently selected from the group consisting of a linear or branched, substituted or unsubstituted, saturated or unsaturated lower alkyl group;

where the aromatic ring of the polyesteramides have from zero to four $Z_1$ substituents, each of which is independently selected from the group consisting of halide, lower alkyl, alkoxy, nitro, alkyl ether, a protected hydroxyl group, a protected amino group and a protected carboxylic acid group; and Y is selected from the group consisting of $$-O-\phantom{}\!\!\bigcirc\!\!\phantom{}^{Z_1}-R-CH-NH-\overset{O}{\underset{\phantom{}}{C}}-R_2-\overset{O}{\underset{\phantom{}}{C}}- \quad \text{or}$$
$$\underset{COOR_1}{\overset{\mid}{\phantom{C}}}$$

$$-NH-CH-R-\phantom{}\!\!\bigcirc\!\!\phantom{}^{Z_1}-O-\overset{O}{\underset{\phantom{}}{C}}-R_2-\overset{O}{\underset{\phantom{}}{C}}-;$$
$$\underset{COOR_1}{\overset{\mid}{\phantom{C}}}$$

where a is 0 to 10;
q is independently 1 to 4;
r is independently 1 to 4; and
s is independently 1 to 5000.

Suitable dihydroxybenzoate (DHB) polymers comprise one or more monomer units having the formula:

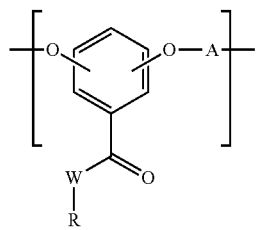

wherein A is selected from the group consisting of C(O), C(O)—R$_1$—C(O), C(=N), C(O)—NH—R$_1$—NH—C(O) or C(S);

W is selected from the group consisting of O, NH or S;

R is selected from the group consisting of hydrogen, an ester or amide protecting group, a leaving group, a linear or branched, substituted or unsubstituted, alkyl, alkenyl, alkynyl, aryl, alkylaryl, alkoxyether, heteroaryl, heteroalkyl or cycloalkyl group having from 1 to 30 carbon atoms, (R$_2$)$_r$O((CR$_3$R$_4$)$_a$O)$_s$(R$_2$)$_r$, a sugar, a pharmaceutically-active moiety, and a biologically-active moiety, where a is independently 1 to 4; b is independently 0 or 1; r is independently to 4; s is independently 1 to 5000;

R$_1$ is independently selected from the group consisting of a divalent, linear or branched, substituted or unsubstituted alkyl, alkenyl, aryl, alkylaryl, alkylene oxide or arylene oxide moiety having from 1 to 30 carbon atoms, (R$_2$)$_r$O ((CR$_3$R$_4$)$_a$O)$_s$(R$_2$)$_r$, and (R$_2$)$_r$CO$_2$((CR$_3$R$_4$)$_a$O)$_s$CO(R$_2$)$_r$, where each a is independently 1 to 4, each r is independently 1 to 4 and s is 1 to 5000;

R$_2$ is independently a linear or branched lower alkyl group; and

R$_3$ and R$_4$ are independently selected from the group consisting of hydrogen and linear or branched lower alkyl group.

Suitable resorcinol-derived polymers comprise monomer units having the formula:

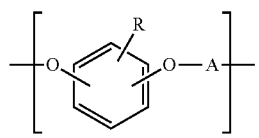

wherein A is selected from the group consisting of C(O), C(O)—R$_1$—C(O), C(=N), C(O)—NH—R$_1$—NH—C(O) or C(S);

R is selected from the group consisting of hydrogen, halo, a linear or branched, substituted or unsubstituted, alkyl, alkenyl, allynyl, aryl, alkylaryl, alkoxyether, heteroaryl, heteroalkyl or cycloalkyl group having from 1 to 30 carbon atoms, (R$_2$)$_b$C(O)OR$_2$, (R$_2$)$_r$O((CR$_3$R$_4$)$_a$O)$_s$(R$_2$)$_r$, a sugar, a pharmaceutically-active compound, and a biologically-active compound, wherein each a is independently 1-4, each b is independently 1 to 4, r is independently 1-4, and each s is independently 1-5000;

R$_1$ is independently selected from the group consisting of a divalent, linear or branched, substituted or unsubstituted alkyl, alkenyl, alkylene oxide or arylene oxide moiety having from 1 to 30 carbon atoms, (R$_2$)$_r$O((CR$_3$R$_4$)$_a$O)$_s$ (R$_2$)$_r$, or (R$_2$)$_r$CO$_2$((CR$_3$R$_4$)$_a$O)$_s$CO(R$_2$)$_r$, where each a is independently 1 to 4, each r is independently 1 to 4 and s is 1 to 5000;

R$_2$ is independently linear or branched lower alkyl; and

R$_3$ and R$_4$ are independently selected from the group consisting of hydrogen, and a linear or branched lower alkyl group.

In a particular embodiment of the invention, the coating comprises about 0.1% to about 25% polyethylene glycol and about 75% to about 99.9% of a polyphenolic polymer, by weight of the combined coating.

In yet another embodiment of the invention, the coating comprises about 10% to about 18% polyethylene glycol and about 72 to about 90% of a polyphenolic polymer, by weight of the combined coating.

The optional drug may be elected from the group consisting of antimicrobial agents, anesthetics, analgesics, anti-inflammatory agents, anti-scarring agents, anti-fibrotic agents and leukotriene inhibitors. In another embodiment of the invention, the drug is an antimicrobial agent selected from the group consisting of antibiotics, antiseptics, and disinfectants. In yet another embodiment, the drug is an antibiotic selected from the group consisting of rifampin, minocycline, silverlchlorhexidine, and combinations thereof. In certain embodiments, the coating comprises both rifampin and minocycline.

In some embodiments, the present invention comprises a medical device coated with a coating comprising a polyethylene glycol, at least one polyphenolic polymer, and optionally at least one drug, wherein the surface of the medical device comprises a material selected from metals, including stainless steel and titanium; organic and/or natural or synthetic polymers including polyethylene, polylactic acid, polyglycolic acid, cellulose, and mixtures of various restorable polymers; and materials from a biological origin including porcine heart valves.

In yet another embodiment of the invention, the medical device is a orthopedic fixation device. In certain embodiments of the invention, the orthopedic fixation device is a screw, tack rod, pin, or plate.

DETAILED DESCRIPTION

Figure 1:
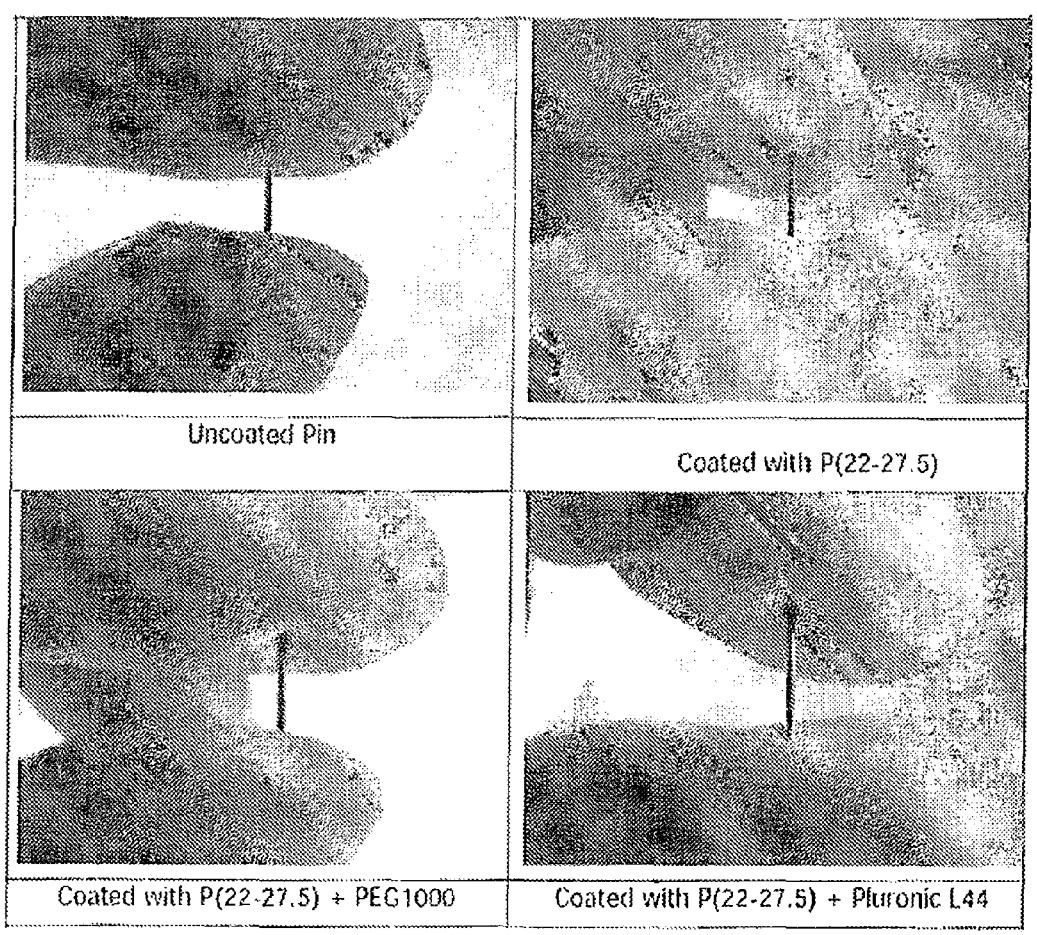
FIG. 1 shows stainless-steel orthopedic pins coated with P(22-27.5), P(22-27.5) and 10% PEG-1000 by weight, or P(22-27.5) and 10% Pluronic L44 by weight as compared to an uncoated pin.

In some embodiments, the coatings of the present invention comprise at least one polyphenolic polymer blended with polyethylene glycol. In other embodiments the coatings of the present invention comprise at least one polyphenolic polymer blended with polyethylene glycol and at least one drug.

In certain embodiments of the invention, suitable polyphenolic polymers are biodegradable polymers such as tyrosine-derived polyarylates, including those polymers described in U.S. Pat. Nos. 4,980,449; 5,099,060; 5,216,115; 5,317,077; 5,587,507; 5,658,995; 5,670,602; 6,048,521; 6,120,491; 6,319,492; 6,475,477; 6,602,497; 6,852,308; 7,056,493; RE37,160E; and RE37,795E; as well as those described in U.S. Patent Publication Nos. 2002/0151668; 2003/0138488; 2003/0216307; 200410254334; 2005/0165203; and those described in PCT Publication Nos. WO99/52962; WO 01/49249; WO 01/49311; WO 03/091337; the disclosures of which are hereby incorporated by reference herein in their entirety. These patents and publications also disclose other polymers containing tyrosine-derived diphenol monomer units or other diphenol monomer units, including polyarylates, polycarbonates, polyiminocarbonates, polythiocarbonates, polyphosphonates and polyethers.

Other polyphenolic polymers suitable for use in the coatings of the present invention include those described in U.S. Patent Publication Nos. US 2010/0015237; US 2010/0130478; US 2010/0074940 (linear polyesteramides from aminophenolic esters); U.S. Patent Publication No. US 2010/0129417 (dihydroxybenzoate polymers); US 2010/0167992; and US 2009/0088548.

Likewise, the foregoing patents and publications describe methods for making these polymers, some methods of which may be applicable to synthesizing other biodegradable polymers.

Polymers

Definitions and Abbreviations

The compounds herein described may have asymmetric (chiral) centers. All chiral, diastereomeric, and racemic forms are included in the present invention. Geometric isomers of olefins and the like can also be present in the compounds described herein, and all such stable isomers are contemplated in the present invention.

By "stable compound" or "stable structure" is meant herein a compound or molecule that is sufficiently robust to survive isolation to a useful degree of purity from a reaction mixture, and for formulation into or use as an efficacious therapeutic agent.

As used herein, unless otherwise clear from the context, "alkyl" means both branched- and straight-chain, saturated aliphatic hydrocarbon groups having the specified number of carbon atoms. Straight and linear are used interchangeably. As used herein "lower alkyl" means an alkyl group having 1 to 6 carbon atoms. When substituted, the substituents can include halide, alkyl, alkoxy, hydroxy, amino, cyano, nitro, trifluoromethyl, trifluoroethyl, additional substituents as described herein, and the like, compatible with the synthesis of the molecules of the invention.

As used herein, "alkenyl" means hydrocarbon chains of either a straight or branched configuration and one or more unsaturated carbon-carbon double bonds, such as ethenyl, propenyl, and the like. "Lower alkenyl" is an alkenyl group having 2 to 6 carbon atoms. As used herein, "alkynyl" means hydrocarbon chains of either a straight or branched configuration and one or more carbon-carbon triple bonds, such as ethynyl, propynyl and the like. "Lower alkynyl" is an alkynyl group having 2 to 6 carbon atoms. When the number of carbon atoms is not specified, then alkyl, alkenyl and alkynyl refers to the respective groups having from 2-20 carbon atoms. Alkylene and alkenylene groups are alkyl groups and alkenyl groups, respectively, which are divalent. When substituted, the substituents can include halide, lower alkyl, alkoxy, hydroxy, amino, cyano, nitro, trifluoromethyl, trifluoroethyl, additional substituents as described herein, and the like compatible with the properties and synthesis of the molecules of the invention.

As used herein, "saturated or unsaturated alkyl" refers to any of an alkyl group, an alkenyl group, or an alkynyl group, having any degree of saturation, i.e., completely saturated (as in alkyl), one or more double bonds (as in alkenyl) or one or more triple bonds (as in alkynyl).

Examples of alkyl groups include but are not limited to, methyl, ethyl, n-propyl, isopropyl, n-butyl, isobutyl, t-butyl, pentyl, hexyl, n-heptyl, n-octyl, isooctyl, nonyl, decyl, and the like; alkylene and alkenylene groups include but are not limited to, methylene, ethylene, propylenes, propenylene, butylenes, butadiene, pentene, n-hexene, isohexene, n-heptene, n-octene, isooctene, nonene, decene, and the like. Those of ordinary skill in the art are familiar with numerous linear and branched hydrocarbon groups. Alkynyl groups include but are not limited to ethynyl and propynyl groups.

As used herein, "aryl" means any stable 6- to 14-membered monocyclic, bicyclic or tricyclic ring, containing at least one aromatic carbon ring, for example, phenyl, naphthyl, indanyl, tetrahydronaphthyl (tetralinyl) and the like. When substituted, the substituents can include halide, alkyl, alkoxy, hydroxy, amino, cyano, nitro, trifluoromethyl, trifluoroethyl, additional substituents as described herein, and the like compatible with the properties and synthesis of the molecules of the invention.

As used herein, "alkylaryl" refers to a moiety in which an aryl group is attached to an alkyl group, which in turn is the attachment point of the substituent. For example, a benzyl ester represents an alkylaryl moiety in which the methylene attached to a phenyl ring is bonded to the oxygen of the ester. The aryl group of this moiety can optionally be substituted in accordance with the definitions herein.

The term "substituted" as used herein means that one or more hydrogens on the designated atom are replaced with a selection from the indicated groups, provided that the designated atom's normal valency is not exceeded, and that the substitution results in a stable compound. If no substituent is indicated then the valency is filled with a hydrogen.

The term "substituted benzyl" refers to benzyl groups substituted with one or more halogens, methoxy groups, nitro groups, alkyl groups, and the like. Substituted benzyl groups known in the art to be suitable for use as protecting groups for ethers and esters are included, including but not limited to 4-methoxybenzyl, 2-methoxybenzyl, 2,4-dimethoxybenzyl, and 2-nitrobenzyl groups.

The terms "radical," "group," "functional group," "moiety," and "substituent" can be used interchangeably in some contexts and can be used together to further describe a chemical structure. For example, the term "functional group" can refer to a chemical "group" or "radical," which is a chemical structure variable that can be in-chain, pendant and/or terminal to the chemical structure. A functional group may be substituted.

A "halide" or a "halo" group is a halogen atom, and includes fluoro, chloro, bromo and iodo groups.

The term "alkoxy" refers to an alkyl group having at least one oxygen substituent represented, for example, by R—O—, where is generally an alkyl group. Suitable alkoxy groups include, without limitation, methoxy, ethoxy, and propoxy.

Examples of poly(alkylene glycols) include, but are not limited to, poly(ethylene oxide)(PEG), poly(propylene glycol) (PPG), poly(tetramethylene glycol), and any derivatives, analogs, homologues, congeners, salts, copolymers and combinations thereof. Poly(alkylene glycols) also include poloxamers (including those sold under the brand name Pluronics® as discussed herein) and those poly(alkylene glycols) having at least one terminal functional other than a hydroxyl group.

Abbreviations used herein for naming polymers and the subunits thereof include DBB, dihydroxybenzoic acid; Bz, benzyl; Et, ethyl; glu, glutarate; Me, methyl; PEG, polyethylene glycol; succ, succinate; Res, resorcinol; dig, diglycolate.

Tyrosine-Based Polyarylates

In some embodiments of the invention, the polyphenolic polymers are comprised of biodegradable tyrosine-derived diphenols co-polymerized with a diacid to form; it is believed, non-toxic bioerodable polyarylates. These polymers have various structural moieties that make them suitable for use with different substrates:

| Aromatic Ring | Hydrophobic | Non polar | Low Energy |
| Alky chains | Hydrophobic | Non polar | Low Energy |
| Amide groups | Hydrophilic | Polar | High Energy |
| Ester groups | Hydrophilic | Polar | High Energy |
| Acid groups | Hydrophilic | Polar | High Energy |
| Phenolic OH | Hydrophilic | Polar | High Energy |

The polyarylates of the present invention are prepared by the condensation of a diacid with a diphenol according to the method described by U.S. Pat. No. 5,216,115, in which diphenol compounds are reacted with aliphatic or aromatic dicarboxylic acids in a carbodiimide mediated direct polyesterification using 4-(dimethylamino)-pyridinium-p-toluene sulfonate (DPTS) as a catalyst. The disclosure of U.S. Pat. No. 5,216,115 is hereby incorporated by reference herein its entirety.

In certain embodiments of the invention, the coating comprises a polyarylate having repeating units with the structure of Formula I:

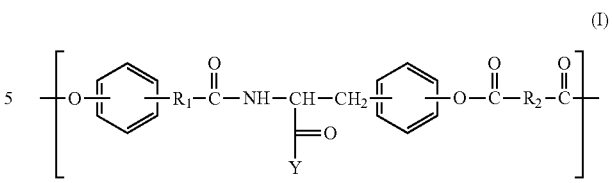

(I)

wherein $R_1$ is independently selected from the group consisting of CH=CH or $(CH_2)_n$, where n ranges from 0 to 18;

Y is selected from the group consisting of $C_1$-$C_{18}$ alkylamino, —OR', —NHCH$_2$CO$_2$R', —NH(CH$_2$)$_q$OR', —NH(CH$_2$CH$_2$O)$_p$R', —NH(CH$_2$CH$_2$CH$_2$O)$_p$R',

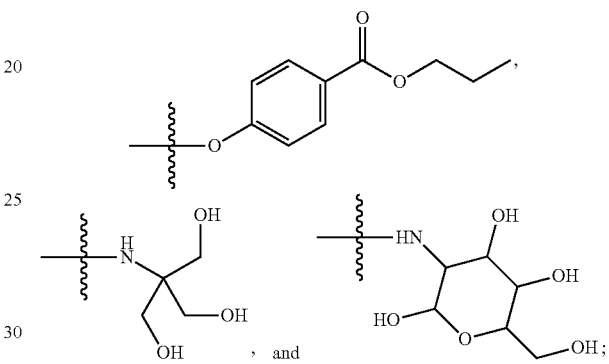

q is 0 to 4;
p is 1 to 5000;
R' is independently selected from the group consisting of H, $C_1$-$C_{18}$ alkyl, $C_2$-$C_{18}$ alkenyl, $C_8$-$C_{14}$ alkylaryl, benzyl, and substituted benzyl;

$R_2$ is independently a divalent, linear or branched, substituted or unsubstituted alkylene, alkenylene, alkynylene, arylene, alkylarylene, alkyl ether or aryl ether moiety having from 1 to 30 carbon atoms; —$(R_5)_qO((CR_3R_4)_rO)_s(R_5)_q$—; or —$(R_5)_qCO_2((CR_3R_4)_rO)_s)CO(R_5)_q$—;

$R_3$ and $R_4$ are independently selected from the group consisting of hydrogen and linear or branched, substituted or unsubstituted alkyl having from 1 to 10 carbon atoms; and $R_5$ is independently selected from a group consisting of a linear or branched, lower alkylene or lower alkenylene.

The diphenol compounds may be selected from the tyrosine-derived diphenol monomers of U.S. Pat. Nos. 5,587,507 and 5,670,602, the disclosures of both of which are also incorporated herein by reference. In some embodiments, the polyarylates of Formula I are prepared using tyrosine-derived diphenol monomers having the structure of Formula II:

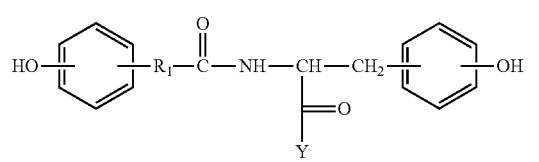

(II)

wherein $R_1$ and Y are the same as described above with respect to Formula I.

In other embodiments of this invention, the diphenol monomers are desaminotyrosyltyrosine carboxylic acids and esters thereof, wherein $R_1$ is —$CH_2CH_2$—, which are referred to herein as DT esters. For purposes of the present invention, the ethyl ester (Y=$OR_2$; $R_2$=ethyl) is referred to as DTE; the benzyl ester (Y=$OR_2$; $R_2$=benzyl) is referred to as DTBn; when Y=—$NH_2$—$CH_2$—$CO_2$—$CH_3$, (glycine methyl ester linked through the amino group of glycine) the compound is referred as DTGM; when Y=$OR_2$ and $R_2$=propyl paraben the compound is referred to as DTPP, and so forth. Both U.S. Pat. Nos. 5,587,507 and 5,670,602 disclose methods by which these monomers may be prepared where these disclosures are hereby incorporated herein by reference. For purposes of the present invention, the desaminotyrosyl-tyrosine free carboxylic acid (Y=OH) is referred to as DT.

It is believed that it may not be possible to polymerize the polyarylates having pendant free carboxylic acid groups from the corresponding diphenols with pendant free carboxylic acid groups without cross-reaction of the free carboxylic acid groups with the co-monomer. Accordingly, polyarylates that are homopolymers or copolymers of benzyl ester diphenyl monomers, such as DTBn, may be converted to corresponding free carboxylic acid homopolymers and copolymers through the selective removal of the benzyl groups by the palladium catalyzed hydrogenolysis method disclosed in U.S. Pat. No. 6,120,491, the disclosure of which is incorporated by reference herein. In most embodiments catalytic hydrogenolysis is necessary because the lability of the polymer backbone prevents the employment of harsher hydrolysis techniques.

In particular embodiments of the invention, the dicarboxylic acids are derived from poly(alkylene oxides) such as polyethylene glycol, polypropylene glycol, polybutylene glycol, Pluronics and the like. In specific embodiments, the diacids are polyethylene glycol diacids.

It is believed that the polyarylates of the present invention degrade by hydrolysis into the original starting materials, i.e., the tyrosine-derived diphenols and the poly(alkylene oxide)dicarboxylic acids. The poly(alkylene oxide)dicarboxylic acids that are poly(alkylene oxides)bis-functionalized with dicarboxylic acids further degrade to the starting poly(alkylene oxides) and dicarboxylic acids.

The polyarylates of the present invention are believed to be highly hydrophilic, which is advantageous for polymeric drug delivery systems. However, the hydrophilic:hydrophobic balance of the polyarylates can be varied in several ways. The ester of the pendant chain of the diphenol can be changed, with longer-chain ester groups increasing hydrophobicity. Increasing the molecular weight of the poly(alkylene oxide) or increasing the number of carbons in the alkylene group of the poly(alkylene oxide) will also increase hydrophobicity. Changing the dicarboxylic acid used to bis-functionalized the poly(alkylene oxide) will also change the hydrophilic:hydrophobic balance.

In some embodiments, the polyarylates have weight average molecular weights between about 1,000 and 500,000 daltons. In other embodiments, the polyarylates have weight average molecular weights between about 3,000 and 50,000 daltons. In yet other embodiments, the polyarylates have weight average molecular weights between about 5,000 and 15,000 daltons. Molecular weights are calculated by gel permeation chromatography relative to polystyrene standards in tetrahydrofuran without further correction.

The molecular weights of the polyarylates can be controlled either by limiting the reaction time or the ratios of either component. Molecular weights can also be controlled by the quantity of the carbodiimide coupling reagent that is used. The viscosities of the polyarylates of the present invention can also be reduced by mixing with water to form either an aqueous solution or emulsion of the polymer.

As used herein, DTE is the diphenol monomer desaminotyrosyl-tyrosine ethyl ester; DTBn is the diphenol monomer desaminotyrosyl-tyrosine benzyl ester; DT is the corresponding free acid form, namely desaminotyrosyl-tyrosine. BTE is the diphenol monomer 4-hydroxy benzoic acid-tyrosyl ethyl ester; BT is the corresponding free acid form, namely 4-hydroxy benzoic acid-tyrosine.

P22 is a polyarylate copolymer produced by condensation of DTE with succinate. P22-10, P22-15, P22-20, P22-xx, etc., each represent copolymers produced by condensation of (1) a mixture of DTE and DT using the indicated percentage of DT (i.e., 10, 15, 20 and xx % DT, etc.) with (2) succinate. The P22 copolymer can contain from about 0-50%, about 5-50%, about 5-40%, about 1-30% or about 10-30% DT, including but not limited to, about 1, about 2, about 5, about 10, about 15, about 20, about 25, about 27.5, about 30, about 35, about 40%, about 45% and about 50% DT.

Additional suitable tyrosine-based polyarylates are copolymers of desaminotyrosyltyrosine (DT) and an desaminotyrosyl-tyrosyl ester (DT ester), wherein the copolymer comprises from about 0.001% DT to about 80% DT and the ester moiety can be a branched or unbranched alkyl, alkylaryl, or alkylene ether group having up to 18 carbon atoms, any group of which can, optionally have a polyalkylene oxide therein. Similarly, another group of suitable polyarylates are the same as the foregoing but the desaminotyrosyl moiety is replaced by a 4-hydroxybenzoyl moiety. In particular embodiments, the DT or BT contents include those copolymers with from about 1% to about 30%, from about 5% to about 30% from about 10 to about 30% DT or BT. Preferred diacids (used informing the polyarylates) include succinate, glutarate and glycolic acid.

Additional biodegradable polymers useful for the present invention are the biodegradable, resorbable polyarylates and polycarbonates disclosed in U.S. provisional application Ser. No. 60/733,988, filed Nov. 3, 2005 and in its corresponding PCT Appln. No. PCT/US06/42944, filed Nov. 3, 2006. These polymers, include, but are not limited to, BTE glutarate, DTM glutarate, DT propylamide glutarate, DT glycineamide glutarate, BTE succinate, BTM succinate, BTE succinate PEG, BTM succinate PEG, DTM succinate PEG, DTM succinate, DT N-hydroxysuccinimide succinate, DT glucosamine succinate, DT glucosamine glutarate, DT PEG ester succinate, DT PEG amide succinate, DT PEG ester glutarate and DT PEG ester succinate.

Additionally, the polyarylate polymers used in the present invention can have from 0.1-99.9% PEG diacid to promote the degradation process as described in U.S. provisional application Ser. No. 60/733,988. In particular embodiments, suitable polyarylates comprise blends of polyarylates, or blends of other biodegradable polymers with polyarylates.

Linear Polyesteramides

The coatings of the present invention may also comprise biodegradable polyesteramides (PEA) polymers. These synthetic polymers comprise one or more repeating units represented by the formula

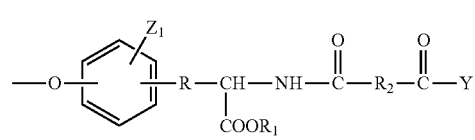

wherein

R is selected from the group consisting of —(CR$_3$R$_4$)$_a$ and —CR$_3$=CR$_4$—;

R$_1$ is selected from the group consisting of hydrogen and saturated or unsaturated alkyl, aryl, alkylaryl or alkyl ether having from 1 to 20 carbon atoms and —(R$_5$)$_q$O((CR$_3$R$_4$)$_r$O)$_s$—R$_6$;

R$_2$ is independently selected from the group consisting of a divalent, linear or branched, substituted or unsubstituted alkylene, alkenylene, alkynylene, arylene, alkylarylene, alkyl ether and aryl ether moiety having from 1 to 30 carbon atoms; —(R$_5$)$_q$O((CR$_3$R$_4$)$_r$O)$_s$(R$_5$)$_q$—; and —(R$_5$)$_q$CO$_2$(CR$_3$R$_4$)$_r$O)$_s$CO(R$_5$)$_q$—;

R$_3$ and R$_4$ are independently selected from the group consisting of hydrogen and linear or branched, substituted or unsubstituted alkyl groups having from 1 to 10 carbon atoms;

R$_5$ is independently selected from the group consisting of a linear and branched, lower alkylene and lower alkenylene groups;

R$_6$ is independently selected from the group consisting of linear and branched, substituted or unsubstituted, saturated or unsaturated lower alkyl group;

where the aromatic ring has from zero to four Z1 substituents, each of which is independently selected from the group consisting of halide lower alkyl, alkoxy, nitro, alkyl ether, a protected hydroxyl group, a protected amino group and a protected carboxylic acid group;

Y is selected from the group consisting of

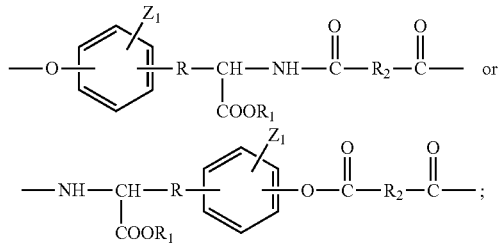

a is 0 to 10;

q is independently 1 to 4;

r is independently 1 to 4; and s is independently 1 to 5000.

These polymers are believed to be biodegradable PEA polymers having aminophenol units and diacid units which can be generally represented by the formula p(-AP-X—)n where n is the actual number or the weight average number of repeat units in the polymer.

The aminophenols (AP) have the structure shown in Formula III:

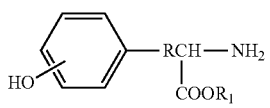

and the diacids (X) have the structure shown in Formula IV:

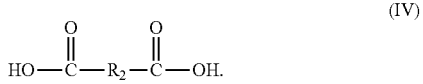

When these monomeric units are polymerized under condensation conditions (or other precursors depending on the synthesis route), the resultant polymers have backbones with both ester and amide bonds, and side chains with ester or free acids (depending on the choice of R$_1$). While the repeat motif of the polymer has the structure AP-X, this simple representation of the polymer does not reflect the various coupling permutations of the aminophenol and the diacid, i.e., whether the coupling between the aminophenol and the diacid occurs via reaction of the AP's amine functional group with one of the acid groups to produce an amide linkage or via reaction of the AP's hydroxyl functional group with one of the acid groups to produce an ester linkage. Hence, the AP-X repeat unit can be represented by the either structure below ("repeat a" or "repeat b", respectively).

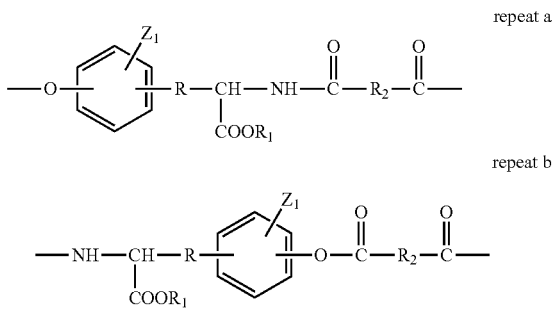

However, this simple structural representation (-AP-X—) does not show the relative relationship of these units to one another since these units can be further joined together by either an amide or ester bond. Hence, the actual structures of the polymers of the present invention which contain the aminophenol and diacid moieties described herein depend on the choice of synthetic route, the choice of coupling agents and the selective reactivity in forming amide or ester bonds.

Accordingly, the polymers of the invention are random copolymers of repeats a and b or strictly alternating copolymers of repeat a, repeat b or both repeats a and b, with the particular polymer structure determined by the method of synthesis as described herein.

For purposes of nomenclature, random copolymers of repeats a and b, are denominated by the simple formula p(-AP-X—), AP-X or as random ab polymers, such names being used interchangeably. Names for this polymer class are based on these representations so that random ab polymers are named for the aminophenol moiety followed by the diacid moiety, regardless of the starting materials. For example, a polymer made by random copolymerization of tyrosine ethyl ester (TB) as the aminophenol moiety with succinic acid as the diacid moiety is referred to as p(TE succinate) or TE succinate. If the diacid moiety were changed to glutaric acid, this random copolymer would be p(TE glutarate) or TE glutarate. For additional clarity or emphasis, the word random may be appended to the polymer name, e.g., TE succinate random or p(1'E succinate) random.

If the polymer is designated without anything after the name, then the polymer is a random copolymer.

There are two strictly alternating copolymer classes that can be obtained from these monomeric units: (1) a linear string of a single repeat, either "repeat a," thus in format (a)n or "repeat b," thus in format (b)$_n$ which are equivalent formats; or (2) a linear string of alternating "repeat a" and "repeat b," thus in form (ab)$_n$ or (ba)$_n$, which are equivalent representations for these polymers. In all cases, n is the number of repeat units. For polymers, n is usually calculated from the average molecular weight of the polymer divided by the molecular weight of the repeat unit.

For purposes of nomenclature, strictly alternating polymers of the (a)$_n$ form are referred to as p(—O-AP-X—) or as alternating "a" polymers. Alternating "a" polymers occur when the reaction conditions are such that the free amine of the aminophenol reacts first with the diacid (or other appropriate reagent) as controlled by the reaction condition, forming an amide linkage and leaving the hydroxyl free for further reaction. For example, a polymer made by copolymerization of tyrosine ethyl ester (TE) as the aminophenol moiety with succinic anhydride (to provide the diacid moiety) leads to an alternating "a" polymer and is referred to herein as p(O-TE succinate) or O-TE succinate.

For purposes of nomenclature, polymers of the (ab), form are referred to as p(-AP-X$_1$-AP-X$_2$), p(AP-X$_1$-AP X$_2$) or as AP-X$_1$-AP X$_2$, when having a and b repeats with different diacids or as "p(-AP-X—) alternating" or as AP-X alternating, when the a and b repeats have the same diacid.

Polymers with two different diacids can be made, for example, by reacting two equivalents of an aminophenol with one equivalent of a first diacid under conditions that favor amide bond formation and isolating the reaction product, a compound having the structure AP-X$_1$-AP, which is also referred to herein as a trimer because it consists of two aminophenol units and one diacid unit. This trimer is reacted with a second diacid under polymerization conditions to produce the polymer p(-AP-X$_1$-AP-X$_2$—) if the second diacid is different from the first diacid, or to produce the polymer p(-AP-X—) alternating if the second diacid is the same as the first diacid. As an illustration, an initial trimer made from TE and succinic acid is denominated as TE-succinate-TE. Reaction of TE-succinate-TE with glutaric acid produces the polymer p(TE-succinate-TE glutarate), whereas reaction with succinic acid produces the polymer p(TE succinate) alternating.

Similarly, p(TE-DG-TE-glutarate) can be made from an initial trimer made from TE and digylcolic acid, TE-DG-TE, which is then reacted with glutaric acid to produce p(TE-DG-TE-glutarate).

The polymers of the invention also include polymers made with mixed aminophenol repeats, mixed diacid repeats and mixed trimer repeats, or any combination of such mixtures. For these complex polymers, the mixed moiety is designated by placing a colon between the names of the two moieties and indicating the percentage of one of the moieties. For example, p(TE:10TBz succinate) random is a polymer made by using a mixture of 90% tyrosine ethyl ester and 10% tyrosine benzyl ester with an equimolar amount of the diacid succinic acid under random synthesis conditions. An example of a strictly alternating (ab)n polymer with a mixed second diacid is p(TE-diglycolate-'1'E 10PEG-bis-succinate:adipate). This polymer is made by preparing the '1'E-diglycolate-TE trimer and copolymerizing it with a mixture of 10% PEG-bissuccinic acid and 90% adipic acid. An example of a strictly alternating (ab), polymer with mixed trimers is p(TE-succinate-TE:35TE-glutarate-TE succinate). This polymer is made by conducting a separate synthesis for each trimer, mixing the isolated trimers in the indicated ratio (65 mol % TE-succinate-TE135 mole % TE-glutarate-TE) and copolymerizing with an equimolar amount of succinic acid.

Other examples of this class of polymers can be found in U.S. Patent Publication No. 2010/0074940.

Dihydroxybenzoate and Resorcinol-Derived Polymers

The coatings of the present invention may also comprise dihydroxybenzoate (DHB) and resorcinol-derived biocompatible, biodegradable and/or resorbable polymers. These polymers are described in detail in U.S. Patent Publication No. 2010/0129417, the disclosure of which is hereby incorporated by reference herein.

The DHB-derived polymers comprise one or more monomer units represented by the formula

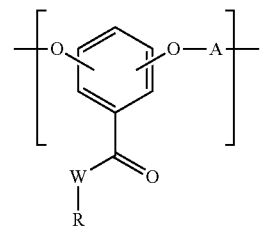

wherein

A is selected from the group consisting of C(O), C(O)—R$_1$—C(O), C(=N), C(O)—NH—R$_1$—NH—C(O) and C(S);

W is selected from the group consisting of O, NH, and S;

R is selected from the group consisting of hydrogen, an ester or amide protecting group, a leaving group, a linear or branched, substituted or unsubstituted, alkyl, alkenyl, alkynyl, aryl, alkylaryl, alkoxyether, heteroaryl, heteroalkyl and cycloalkyl group having from 1 to 30 carbon atoms, (R$_2$)$_r$O((CR$_3$R$_4$)$_a$O)$_s$(R$_2$)$_r$, a sugar, a pharmaceutically-active compound, and a biologically-active compound, wherein each a is independently 1 to 4, each b is independently 0 or 1, r is independently 1 to 4, and each s is independently 1 to 5000;

R$_1$ is independently selected from the group consisting of a divalent, linear or branched, substituted or unsubstituted alkyl, alkenyl, aryl, alkylaryl, alkylene oxide and arylene oxide moiety having from 1 to 30 carbon atoms, (R$_2$)$_r$O ((CR$_3$R$_4$)$_a$O)$_s$(R$_2$)$_r$, or (R$_2$)$_r$CO$_2$((CR$_3$R$_4$)$_a$O)$_s$CO(R$_2$)$_r$, where each a is independently 1 to 4, each r is independently 1 to 4 and s is 1 to 5000;

R$_2$ is independently selected from the group consisting of linear and branched lower alkyl; and R$_3$ and R$_4$ are independently selected from the group consisting of hydrogen and linear or branched lower alkyl.

In some embodiments, the DHB-derived polymers are those in which W is O; A is C(O)—R$_1$—C(O); R is selected from the group consisting of hydrogen, a linear or branched, substituted or unsubstituted, alkyl, alkenyl, alkynyl, aryl, alkylaryl or alkoxyether group having from 1 to 30 carbon atoms, and (R$_2$)$_r$O((CR$_3$R$_4$)$_a$O)$_s$R$_2$)$_r$; and each R$_1$ is, independently selected from the group consisting of a divalent, linear or branched, substituted or unsubstituted alkyl having from 1 to 30 carbon atoms, (R$_2$)$_r$O((CR$_3$R$_4$)$_a$O)$_s$(R$_2$)$_r$, or (R$_2$)$_r$CO$_2$((CR$_3$R$_4$)$_a$O)$_s$CO(R$_2$)$_r$.

The resorcinol-derived polymers comprise one or more monomer units represented by the formula

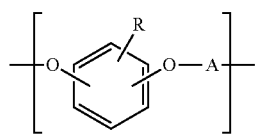

wherein

A is selected from the group consisting of C(O), C(O)—R$_1$—C(O), C(=N), C(O)—NH—R$_1$—NH—C(O) or C(S);

R is selected from the group consisting of hydrogen, halo, a linear or branched, substituted or unsubstituted, alkyl, alkenyl, alkynyl, aryl, alkylaryl, alkoxyether, heteroaryl, heteroalkyl or cycloalkyl group having from 1 to 30 carbon atoms, (R$_2$)$_r$O((CR$_3$R$_4$)$_a$O)$_s$(R$_2$)$_r$, a sugar, a pharmaceutically-active moiety, or a biologically-active moiety, wherein each a is independently 1 to 4, each b is independently 1 to 4, r is independently 1 to 4, and each s is independently 1 to 5000.

R$_1$ is independently selected from the group consisting of a divalent, linear or branched, substituted or unsubstituted alkyl, alkenyl, alkylene oxide or arylene oxide moiety having from 1 to 30 carbon atoms, (R$_2$)$_r$O((CR$_3$R$_4$)$_a$O)$_s$(R$_2$)$_r$, or (R$_2$)$_r$CO$_2$((CR$_3$R$_4$)$_a$O)$_s$CO(R$_2$)$_r$, where each a is independently 1 to 4, each r is independently 1 to 4 and s is 1 to 5000;

R$_2$ is independently selected from the group consisting of linear or branched lower alkyl; and R$_3$ and R$_4$ are independently selected from the group consisting of hydrogen, and linear or branched lower alkyl.

Resorcinol-derived polymers include those in which A is C(O)—R$_1$—C(O); R is hydrogen or a linear or branched, substituted or unsubstituted alkyl group having from 1 to 30 carbon atoms; and each R$_1$ is, independently selected from the group consisting of a divalent, linear or branched, substituted or unsubstituted alkyl having from 1 to 30 carbon atoms, (R$_2$)$_r$O((CR$_3$R$_4$)$_a$O)$_s$(R$_2$)$_r$, or (R$_2$)$_r$CO$_2$((CR$_3$R$_4$)$_a$O)$_s$CO(R$_2$)$_r$.

The nomenclature associated with these polymers has a first part that identifies the polyphenolic moiety (DHB or resorcinol derivatives) and a second part that identifies the A portion of the repeating unit.

If the first part of the monomer unit is an ester or amide, or a substituent, that group is generally listed first in the abbreviations. Hence, MeDHB is the ester form, namely dihydroxybenzoate methyl ester. When a free acid is present (rather than or in addition to an ester), there is no need for an initial group. Thus, DHB is the free acid form.

The second part of the name identifies the group with which the polyphenolic moiety is polymerized, such as the diacid, the carbonate, the iminocarbonate and the like. Hence, specific examples include poly(DHB glutarate), poly(DHB carbonate) and the like.

If a mixture of polyphenol moieties or of copolymerized groups (such as two diacids) are present in the polymer, then that part of the name may include the designation "co" or may have a hyphen, along with an indication of percentage of one of the two moieties. For example, poly(MeDHB:10DHB-co-succinate) and poly(MeDHB-10-DT succinate) can be used interchangeably to mean a polymer made by copolymerizing a mixture of 90% dihydroxybenzoate methyl ester and 10% dihydroxybenzoic acid with the diacid succinic acid. An example of a mixed diacid is poly(MeDHB-co-50:50 PEG600-bis-glutarate glutarate).

Other examples of this class of polymers can be found in U.S. Patent Publication No. 201010129417, the disclosure of which is hereby incorporated by reference herein.

In some embodiments of the invention, the polyphenolic polymer is present at about 80% to about 90% by weight, based on the combined weight of the polyethylene glycol (or pluronic or similar compound) and polyphenolic polymer. In other embodiments, the polyphenolic polymer is present at about 80% by combined weight. In other embodiments, the polyphenolic polymer is present at about 81% by combined weight. In other embodiments, the polyphenolic polymer is present at about 82% by combined weight. In other embodiments, the polyphenolic polymer is present at about 83% by combined weight. In other embodiments, the polyphenolic polymer is present at about 84% by combined weight. In other embodiments, the polyphenolic polymer is present at about 85% by combined weight. In other embodiments, the polyphenolic polymer is present at about 86% by combined weight. In other embodiments, the polyphenolic polymer is present at about 87% by combined weight. In other embodiments, the polyphenolic polymer is present at about 88% by combined weight. In other embodiments, the polyphenolic polymer is present at about 89% by combined weight. In other embodiments, the polyphenolic polymer is present at about 90% by combined weight.

PEG

In the coatings of the present invention, the polyphenolic polymers described above can be blended with, polyethylene glycol (PEG), Pluronic® polymers/copolymers (poloxamers or nonionic triblock copolymers composed of a central hydrophobic chain of polyoxypropylene flanked by two hydrophilic chains of polyoxyethylene), or similar compounds (collectively referred to herein as "PEG" or "polyethylene glycol"). Pluronic® polymers are available from BASF (Florham Park, N.J.), and include block copolymers based on ethylene oxide and/or propylene oxide. The PEGs utilized as part of the present invention may have any molecular weight and those of skill in the art will be able to select a suitable PEG to provide for the desired outcome.

In some embodiments, the PEGs have at least one terminal functional group other than a terminal hydroxyl group. For example, the PEGs may have at least one terminal functional group comprising an ether, for example a methyl ether group.

Suitable PEGs include, but are not limited to, PEG-400 (a low molecular weight grade of PEG having, generally, a molecular weight between about 380 and about 420 g/mol), PEG-1000 (having a molecular weight between about 950 and about 1050 g/mol), and PEG-3350 (having a molecular weight between about 3200 and about 3500 g/mol).

PEG-Acid

In some embodiments, the PEG, Pluronic®, or similar compound is present at about 2% to about 50% by weight, based on the combined weight of the polyethylene glycol (or Pluronic® or similar compound) and polyphenolic polymer, e.g., about 2% by weight, about 4% by weight, about 6% by weight, about 8% by weight, about 10% by weight, about 11% by weight, about 12% by weight, about 13% by weight, about 14% by weight, about 15% by weight, about 16% by weight, about 17% by weight, about 18% by weight, about 19% by weight, about 20% by weight, about 22% by weight, about 24% by weight, about 26% by weight, about 28% by weight, about 30% by weight, about 32% by weight, about 34% by weight, about 36% by weight, about 38% by weight, about 40% by weight, about 42% by weight, about 44% by weight, about 46% by weight, about 48% by weight, or about 50% by weight.

Drugs

The presence of a drug in the coatings of the present invention is optional. However, when a drug is present, any drug, biological agent or active ingredient compatible with the process of depositing the coating onto the surface of a medical device can be incorporated into coatings of the present invention. Doses of such drugs and agents are known to those of ordinary skill in the art. Those of skill in the art can readily determine the amount of a particular drug to include in the coatings on the meshes of the invention.

Examples of drugs suitable for use with the present invention include anesthetics, antibiotics (antimicrobials), anti-inflammatory agents, fibrosis-inhibiting agents, anti-scarring agents, leukotriene inhibitors/antagonists, cell growth inhibitors and the like, as well as combinations thereof. As used herein, "drugs" is used to include all types of therapeutic agents, whether small molecules or large molecules such as proteins, nucleic acids and the like. The drugs of the invention can be used alone or in combination.

Any pharmaceutically acceptable form of the drugs of the present invention can be employed in the present invention, e.g., a free base or a pharmaceutically acceptable salt or ester thereof pharmaceutically acceptable salts, for instance, include sulfate, lactate, acetate, stearate, hydrochloride, tartrate, maleate, citrate, phosphate and the like.

Examples of non-steroidal anti-inflammatories include, but are not limited to, naproxen, ketoprofen, ibuprofen as well as diclofenac; celecoxib; sulindac; diflunisal; piroxicam; indomethacin; etodolac; meloxicam; r-flurbiprofen; mefenamic; nabumetone; tolmetin, and sodium salts of each of the foregoing; ketorolac bromethamine; ketorolac bromethamine tromethamine; choline magnesium trisalicylate; rofecoxib; valdecoxib; lumiracoxib; etoricoxib; aspirin; salicylic acid and its sodium salt; salicylate esters of alpha, beta, gamma-tocopherols and tocotrienols (and all their D, f, and racemic isomers); and the methyl, ethyl, propyl, isopropyl, n-butyl, sec-butyl, t-butyl, esters of acetylsalicylic acid.

Examples of anesthetics include, but are not limited to, lidocaine, bupivacaine, and mepivacaine. Further examples of analgesics, anesthetics and narcotics include, but are not limited to acetaminophen, clonidine, benzodiazepine, the benzodiazepine antagonist flumazenil, lidocaine, tramadol, carbamazepine, meperidine, zaleplon, trimipramine maleate, buprenorphine, nalbuphine, pentazocain, fentanyl, propoxyphene, hydromorphone, methadone, morphine, levorphanol, and hydrocodone. Local anesthetics have weak antibacterial properties and can play a dual role in the prevention of acute pain and infection.

Examples of antimicrobials include, but are not limited to, triclosan, chlorhexidine, rifampin, minocycline (or other tetracycline derivatives), vancomycin, daptomycin, gentamycin, cephalosporins and the like. In particular embodiments the coatings contain rifampin and another antimicrobial agent, for example a tetracycline derivative. In another preferred embodiment, the coatings contain a cephalosporin and another antimicrobial agent. Preferred combinations include rifampin and minocycline, rifampin and gentamycin, and rifampin and minocycline. As used herein, the term antibiotic and antibacterial can be used interchangeably with the term antimicrobial.

Further antimicrobials include aztreonam; cefotetan and its disodium salt; loracarbef; cefoxitin and its sodium salt; cefazolin and its sodium salt; cefaclor; ceflibuten and its sodium salt; ceftizoxime; ceftizoxime sodium salt; cefoperazone and its sodium salt; cefuroxime and its sodium salt; cefuroxime axetil; cefprozil; ceftazidime; cefotaxime and its sodium salt; cefadroxil; ceftazidime and its sodium salt; cephalexin; cefamandole nafate; cefepime and its hydrochloride, sulfate, and phosphate salt; cefdinir and its sodium salt; ceftriaxone and its sodium salt; cefixime and its sodium salt; cefpodoxime proxetil; meropenem and its sodium salt; imipenem and its sodium salt; cilastatin and its sodium salt; azithromycin; clarithromycin; dirithromycin; erythromycin and hydrochloride, sulfate, or phosphate salts ethylsuccinate, and stearate forms thereof; clindamycin; clindamycin hydrochloride, sulfate, or phosphate salt; lincomycin and hydrochloride, sulfate, or phosphate salt thereof; tobramycin and its hydrochloride, sulfate, or phosphate salt; streptomycin and its hydrochloride, sulfate, or phosphate salt; vancomycin and its hydrochloride, sulfate, or phosphate salt; neomycin and its hydrochloride, sulfate, or phosphate salt; acetyl sulfisoxazole; colistimethate and its sodium salt; quinupristin; dalfopristin; amoxicillin; ampicillin and its sodium salt; clavulanic acid and its sodium or potassium salt; penicillin G; penicillin G benzathine, or procaine salt; penicillin G sodium or potassium salt; carbenicillin and its disodium or indanyl disodium salt; piperacillin and its sodium salt; ticarcillin and its disodium salt; sulbactam and its sodium salt; moxifloxacin; ciprofloxacin; ofloxacin; levofloxacins; norfloxacin; gatifloxacin; trovafloxacin mesylate; alatrofloxacin mesylate; trimethoprim; sulfamethoxazole; demeclocycline and its hydrochloride, sulfate, or phosphate salt; doxycycline and its hydrochloride, sulfate, or phosphate salt; minocycline and its hydrochloride, sulfate, or phosphate salt; tetracycline and its hydrochloride, sulfate, or phosphate salt; oxytetracycline and its hydrochloride, sulfate, or phosphate salt; chlortetracycline and its hydrochloride, sulfate, or phosphate salt; metronidazole; dapsone; atovaquone; rifabutin; linezolide; polymyxin B and its hydrochloride, sulfate, or phosphate salt; sulfacetamide and its sodium salt; and clarithromycin.

Examples of antifungals include amphotericin B; pyrimethamine; flucytosine; caspofungin acetate; fluconazole; griseofulvin; terbinafin and its hydrochloride, sulfate, or phosphate salt; ketoconazole; micronazole; clotrimazole; econazole; ciclopirox; naftifine; and itraconazole.

Other drugs that can be incorporated into the coatings on the mesh pouches of the invention include, but are not limited to, keflex, acyclovir, cephradine, malphalen, procaine, ephedrine, adriamycin, daunomycin, plumbagin, atropine, quinine, digoxin, quinidine, biologically active peptides, cephradine, cephalothin, cis-hydroxy-L-proline, melphalan, penicillin V, aspirin, nicotinic acid, chemodeoxycholic acid, chlorambucil, paclitaxel, sirolimus, cyclosporins, 5-flurouracil and the like.

Examples of anti-inflammatory compound include, but are not limited to, anecortive acetate; tetrahydrocortisol, 4,9(11)-pregnadien-17.alpha.,21-diol-3,20-dione and its -21-acetate salt; 11-epicortisol; 17.alpha.-hydroxyprogesterone; tetrahydrocortexolone; cortisona; cortisone acetate; hydrocortisone; hydrocortisone acetate; fludrocortisone; fludrocortisone acetate; fludrocortisone phosphate; prednisone; prednisolone; prednisolone sodium phosphate; methylprednisolone; methylprednisolone acetate; methylprednisolone, sodium succinate; triamcinolone; triamcinolone-16,21-diacetate; triamcinolone acetonide and its -21-acetate, -21-disodium phosphate, and -21-hemisuccinate forms; triameinolone benetonide; triamcinolone hexacetonide; fluocinolone and fluocinolone acetate; dexamethasone and its -21-acetate, -21-(3,3-dimethylbutyrate), -21-phosphate disodium salt, -21-diethylaminoacetate, -21-isonicotinate, -21-dipropionate, and -21-palmitate forms; betamethasone and its -21-acetate, -21-adamantoate, -17-benzoate, -17,21-dipropionate, -17-valerate, and -21-phosphate disodium salts; beclomethasone; beclomethasone dipropionate; diflorasone; diflorasone diacetate; mometasone furoate; and acetazolamide.

Examples of leukotriene inhibitors/antagonists include, but are not limited to, leukotriene receptor antagonists such as acitazanolast, iralukast, montelukast, pranlukast, verlukast, zafirlukast, and zileuton.

Another useful drug that can be incorporated into the coatings of the invention is sodium 2-mercaptoethane sulfonate (Mesna). Mesna has been shown to diminish myofibroblast formation in animal studies of capsular contracture with breast implants [Ajmal et al. (2003) Plast. Reconstr. Surg. 112:1455-1461] and may thus act as an anti-fibrosis agent.

Those of ordinary skill in the art will appreciate that any of the foregoing disclosed drugs can be used in combination with or mixed with coatings of the present invention.

In some embodiments, the present invention comprises polyethylene glycol, a polyphenolic polymer, and rifampin. In other embodiments, the present invention comprises polyethylene glycol, a polyphenolic polymer, and minocycline. In yet other embodiments, the present invention comprises polyethylene glycol, a polyphenolic polymer, and rifampin and minocycline.

In some embodiments, at least one drug is present at about 20% to about 70% of the combined weight of the polyethylene glycol (or pluronic or similar compound), the polyphenolic polymer, and the drug, e.g. about 20% by weight, about 25% by weight, about 30% by weight, about 35% by weight, about 40% by weight, about 45% by weight, about 50% by weight, about 55% by weight, about 60% by weight, about 65% by weight, or about 70% weight.

In other embodiments, wherein at least one drug is present at about 20% to about 70% of the combined weight of the polyethylene glycol (or pluronic or similar compound), the polyphenolic polymer, and the drug, the polyethylene glycol (or pluronic or similar compound) is present at about 3% to about 16% of the combined weight of the polyethylene glycol, the polyphenolic polymer, and the drug, e.g about 3% by weight, about 4% by weight, about 5% by weight, about 6% by weight, about 7% by weight, about 8% by weight, about 9% by weight, about 10% by weight, about 11% by weight, about 12% by weight, about 13% by weight, about 14% by weight, about 15% be weight, or about 16% by weight.

In particular embodiments of the invention wherein at least one drug is present at about 20% to about 70% of the combined weight of the polyethylene glycol (or pluronic or similar compound), the polyphenolic polymer, and the drug, the polyphenolic polymer is present at about 20% to about 75% of the of the combined weight of the polyethylene glycol, the polyphenolic polymer, and the drug, e.g. about 20% by weight, about 25% by weight, about 30% by weight, about 35% by weight, about 40% by weight, about 45% by weight, about 50% by weight, about 55% by weight, about 60% by weight, about 65% by weight, about 70% by weight or about 75% by weight.

Medical Devices

The coatings of the present invention can be used to coat a variety of different types of medical devices including implantable prostheses used to reconstruct, reinforce, bridge, replace, repair, support, stabilize, position or strengthen any soft tissue defect.

Suitable medical devices are known in the art and may include a device having any shape, size, and function. Suitable medical devices may be constructed from any material known in the art and suitable for the particular end use sought.

In some embodiments, the medical devices comprise a material selected from a metal including stainless steel and titanium. In other embodiments, the medical device comprises an organic material and/or a natural or synthetic polymer, including polyethylene, polylactic acids, polyglycolic acids, and cellulose. For example, one polymer which may be utilized is available from MAST Biosurgery, and which is particularly useful for hard tissue (bone) and soft tissue applications, and which comprises Polylactide, which is a copolymer of 70:30 Poly(L-lactide-co-D,L-lactide). Other bioresorable polymers are available from Boehringer Ingelheim, and include the Resomer® family of polylactide-based copolymers. In yet other embodiments, the medical device is comprises of a material from biological origin, such as materials from porcine origin (e.g. porcine heart valves). In other embodiments, the medical devices may be comprised of AlloDerm® Regenerative Tissue Matrix or Strattice™ Reconstructive Tissue Matrix, both of which are available from LifeCell.

Prostheses comprising the coating of the present invention may be used to repair soft tissue defects including hernias, such as, but not limited to inguinal, femoral, umbilical, abdominal, incisional, intramuscular, diaphragmatic, abdomino-thoracic and thoracic hernias.

The coated prostheses can also be used for structural reinforcement for muscle flaps, to provide vascular integrity, for ligament repair/replacement and for organ support/positioning/repositioning such as done with a bladder sling, a breast lift, or an organ bag/wrap. The prostheses can be used in reconstruction procedures involving soft tissue such as an orthopaedic graft support/stabilization, as supports for reconstructive surgical grafts and as supports for bone fractures. The prostheses are generally meshes, membranes or patches, and include woven or non-woven meshes and the like.

Additionally, the coatings of the present invention can be used to coat wound closure adjuncts, such as staples, sutures, tacks, rings, screws, and the like. Likewise, the coatings may provide a barrier function, preferably a temporary biodegradable barrier, which prevents or mitigates contact or adhesion between a substrate (e.g. medical device) and surrounding materials or tissue.

In some embodiments, the coatings of the present invention are capable of conforming to flexible and/or deformable substrates (e.g. collapsible stents, sutures, and the like), preferably without damaging the coating or altering the release of the optional drug from the coating. Similarly, the coating can act to stiffen a device, including a deformable substrate, into a predetermined shape. It is believed that as the coating biodegrades, the stiffness imparted may lesion and the device may assume a second, different shape or stiffness.

The coatings of the present invention can also be used to coat meshes which are formed into or to form pouches, coverings, pockets and the like for implantable medical devices. Such implantable medical devices include, but are not limited to cardiac rhythm management devices such as a pacemaker, a defibrillator, a pulse generator as well as other implantable devices such as implantable access systems, neurostimulators, spinal cord stimulators, breast implants or any other implantable medical device. The coverings, pouches, pockets and the like hence can serve to secure those devices in position, provide pain relief, inhibit scarring or fibrosis, inhibit or prevent bacterial growth or infection (or, more particularly, prevent microbial colonization of a substrate of bacteria), and deliver other drugs to the site of implantation.

In some embodiments, the coated devices may be used to prevent, treat or mitigate bacterial colonization. In some embodiments, the coating comprises an antimicrobial agent, such that the antimicrobial agent may be eluted over time. In some embodiments, the coating comprises minocycline, rifampin, or a mixture of minocycline and rifampin. In some embodiments, the antimicrobial agent is eluted from the coating over time. In other embodiments, the antimicrobial agent is eluted over a period of at least 24 hours. In yet other embodiments, the cumulative release of antimicrobial agent is at least about 30% over 24 hours. In yet further embodiments, the cumulative release of antimicrobial agent is at least about 40% over 24 hours. In yet other embodiments, the cumulative release of antimicrobial agent is at least about 50% over 25 hours. In yet further embodiments, at least about 80% of the antimicrobial agent is released after 3 days.

The coatings of the present invention can also be used in conjunction with any implantable or insertable medical devices which has a temporary, or some time-limited therapeutic need as well as those with permanent function (such as joint replacements).

Other examples of medical devices on which the coating compositions described herein can be coated include, but are not limited to catheters (e.g., renal or vascular catheters such as balloon catheters), guide wires, balloons, filters (e.g., vena cava filters), stents (including coronary vascular stents, cerebral, urethral, ureteral, biliary, tracheal, gastrointestinal and esophageal stents), stent grafts, cerebral aneurysm filler coils (including Guglilmi detachable coils and metal coils), vascular grafts, myocardial plugs, femoral plugs, patches, pacemakers and pacemaker leads, heart valves, vascular valves, biopsy devices, patches for delivery of therapeutic agent to intact skin and broken skin (including wounds); tissue engineering scaffolds for cartilage, bone, skin and other in vivo tissue regeneration; sutures, suture anchors, anastomosis clips and rings, tissue staples and ligating clips at surgical sites; orthopedic fixation devices such as interference screws in the ankle, knee, and hand areas, tacks for ligament attachment and meniscal repair, rods and pins for fracture fixation, screws and plates for cranionaxillofacial repair; dental devices such as void fillers following tooth extraction and guided-tissue-regeneration membrane films following periodontal surgery; and various coated substrates that are implanted or inserted into the body.

In yet other embodiments, the coatings may be applied to the dressings used in negative pressure wound therapy. Dressings used in such a therapy include foams (open and closed cell foams), meshes, gauzes, or other textiles having a textured or dimpled wound contact surface. In some embodiments, suitable dressings include V.A.C. Simplace Dressings, V.A.C. Granufoam Bridge Dressings, V.A.C. Abdominal Dressing System, and V.A.C. WhiteFoam Dressings, available from Kinetic Concepts, Inc. (San Antonio, Tex.). In other embodiments, suitable dressings include those from Smith & Nephew and sold under the brand names RENASYS-F Foam and RENASYS-G Gauze (St. Petersburg, Fla.). In yet other embodiments, suitable dressings include those available from Prospea (Fort Worth, Tex.).

The coating may be applied to any surface of the negative pressure wound therapy dressing. In some embodiments, the coating at least partially covers the surface of the dressing which is in contact with the wound, incision, etc. of the subject. In some embodiments, the coating applied to the negative pressure wound therapy dressing includes at least one drug. In other embodiments, the coating applied to the negative pressure wound therapy dressing includes at least one antimicrobial compound. In yet other embodiments, the coating applied to the negative pressure wound therapy dressing includes rifampin and minocycline. It is believed that the drug included in any coating applied to a dressing may be eluted over a predetermined time period such that effective amounts of the drug are administered to the wound or incision of the subject. It is further believed that the inclusion of an antimicrobial compound in the dressing coating could prevent, treat, or mitigate any infections present in the wound or incision.

Accordingly, the present invention provides methods of treating a disorder or condition in a patient comprising implanting a medical device or a medical device assembly coated with a coating composition of the present invention, e.g., as a coating, in conjunction with a covering or as the complete or partial device, by implanting the device in a patient, and particularly for disorders and conditions such as a cardiovascular disorder, a neurological disorder, a hernia or hernia-related disorder, an ophthalmic condition, or anatomical repair, reconstruction, replacement or augmentation.

In some embodiments, the method is used to implant a stent to treat atherosclerosis, thrombosis, restenosis, periodontitis, hemorrhage, vascular dissection or perforation, vascular aneurysm, vulnerable plaque, chronic total occlusion, claudication, anastomotic proliferation for vein and artificial grafts, bile duct obstruction, ureter obstruction, tumor obstruction, or combinations thereof In other embodiments, the coating compositions of the present invention can be used as part of a method to implant a medical device for local delivery of drugs, such as nerve growth factors to stimulate nerve regeneration or chemotherapeutic agents to treat cancer. In yet another embodiment of the invention, coated punctual plugs can be used for ocular delivery.

In other embodiments, the coating compositions of the present invention can be used as part of a method to implant a surgical mesh to reconstruct, reinforce, bridge, replace, repair, support, stabilize, position or strengthen any soft tissue defect, including a hernia.

In yet other embodiments, the coating compositions of the present invention can be used as part of a method to implant a medical device assembly such as a CRM in a covering or pouch, a neurostimulator in a pouch or covering, or a breast implant in a pouch or covering.

Application

The compositions of the present invention may be applied to the surface (interior or exterior) of a medical device by any suitable technique known in the art. In a particular embodiment of the invention the coating composition is sprayed onto the surface of the device. In yet another embodiment of the invention, the device is dipped into the coating composition.

In a certain embodiment of the invention, the coating is cured after application by any suitable technique known in the art, including, but not limited to, exposure to ultraviolet radiation, electron beams, microwave beams or heat. In a particular embodiment of the invention, the polymer coating is cured at about 40° to about 70° C. under vacuum.

In another embodiment of the invention, the coating is cast into a sheet, this sheet is then placed on to the device, and the coating is adhered to the device by curing. In a particular embodiment of the invention, this curing can take place at about 40° to about 70° C. under vacuum.

In a further embodiment of the invention, the coating is cast into a tube, the device is then placed in the tube, and the coating is adhered to the device by curing. In a certain embodiment of the invention, this curing can take place at about 40° to about 70° C. under vacuum.

This approach of first manufacturing films comprising the compositions of the present invention, then applying such films to a device or substrate can be advantageous in simplifying quality control (e.g., by allowing the manufacture of a single lot of film which can be qualified by a single quality control test, whereas direct coating of various a batches of devices may require multiple quality control tests), or by allowing the coating to be custom-fitted to the device during a medical procedure. The degree of stickiness of the coating can also be adjusted by modifying the type of PEG polymer used in the composition. For example, stickier coatings are provided by the use of PEG, whereas reduced levels of stickiness can be obtained using copolymers of polyethylene oxide/polypropylene oxide, such as PLURONIC polymers. Less sticky coatings can be useful in situations where there may be a need to remove the coating. In a particular embodiment of the invention, wherein the coating comprises PLURONIC, an applied coating can be removed and/or replaced.

In yet another embodiment of the invention, an orthopedic pin can be coated with the coating of the present invention and then be cut to the appropriate size for insertion.

In some embodiments, the medical device is at least partially covered by the coatings of the present invention. In other embodiments, at least about 25% of the surface of the medical device is covered by the coatings of the present invention. In yet other embodiments, at least about 30% of the surface of the medical device is covered by the coatings of the present invention. In yet further embodiments, at least about 40% of the surface of the medical device is covered by the coatings of the present invention.

Medical Applications

As discussed above infections after total joint arthroplasty represent a clinically devastating complication. These infections are exceeding difficult to treat because the implanted materials provide avascular surfaces to which bacteria adhere and form biofilms, which block the penetration of immune cells and antibiotics. A medical device coated with an antibiotic impregnated coating containing minocycline and rifampin effectively reduces infection, decreases inflammation and prevents biofilm formation on implants.

The antibiotic-impregnated bioresorbable tyrosine-derived polymer coatings of the present invention, such as P22-27.5 blended with PEG400, which slowly elute minocycline and rifampin, are clinically effective in reducing bacterial load, preventing the infection, decreasing neutrophil infiltration/inflammation and preventing biofilm formation on the implants.

A previous study in a rabbit intramedullary screw $S.$ $aureus$ osteomyelitis model found that minocycline and rifampin sprayed onto the implant without an elution polymer was only partially effective in preventing colonization of the implant and infection of the bone. The polymer coating of the present invention is more effective at preventing bacterial infection, and therefore the subsequent complications, than previously used methods which do not allow for continuous, extended release of drugs after implantation. These results suggest that this coating can be used to prevent infections associated with the use of orthopedic implants. It will be appreciated by those skilled in the art that various omissions, additions and modifications may be made to the invention described above without departing from the scope of the invention, and all such modifications and changes are intended to fall within the scope of the invention, as defined by the appended claims. All references, patents, patent applications or other documents cited are herein incorporated by reference in their entirety for all purposes.

EXAMPLES

The coatings are described based on the polymer content of the coating. For example, a coating wherein 90% of the polymer content is P(22-27.5) and 10% is PEG-1000 and would be described as "P(22-27.5):10% PEG-1000".

I. Coating

A. Preparation of Coating Solution without Drug

P22-27.5 (0.85 g) and PEG 1000 (0.15 g) were weighted into a 20 mL clean amber vial. 3.5 mL of dichloromethane and 1.5 mL of methanol were added, then the mixture was shaken to dissolve the components using a vortex shaker. The mixture was filtered and the solution was transferred into a clean 7 mL scintillation vial using a polypropylene syringe fitted with a 1 micron syringe filter. The vial was capped and let stand at least 5 minutes before use.

B. Preparation of Coating Solution with Drug

P22-27.5 (0.85 g), PEG-1000 (0.15 g), Rifampin (0.40 g) and Minoeycline HCL (0.4 g) were weighted into a 20 mL clean amber vial. 3.5 mL dichloromethane and 1.5 mL methanol were added and then the mixture was shaken to dissolve the components using a vortex shaker. When the solution was clear, it was filtered into a clean 7 mL scintillation vial using a polypropylene syringe fitted with a 1 micron syringe filter. The vial was capped and let stand for at least 5 minutes before use.

C. Dipping Procedure for 1 Inch Pin

A minimum portion (about 2 mm) of the pin was inserted into a 200 µL pipette tip. The exposed side of the pin was manually dipped into the prepared solution (at least ¾ of the pin surface should be covered by the solution). The pin was slowly raised from the solution and left on the pipette tip until it dried. The pin was carefully removed from the pipette tip, reversed, and the coated side was inserted into the pipette tip. The uncoated portion of the pin was again inserted into the prepared solution. Slowly the pin was raised and left on the 200 pL pipette tip until it was dry. If more coating needed to be added onto the cut end of the pin, the procedure could be repeated. The pins were dried under vacuum until acceptable solvent levels were obtained. The pins were stored in tightly sealed containers at ~15 C.

D. Automated Dipping Procedure

A minimum portion (about 2 mm) of the pin was inserted into a 200 µL pipette tip as described above. The pipette was screwed onto an aluminum stem made for the diptech coating machine. The stem was inserted into the platform of diptech coating machine. The machine was started and cyclic dipping of the pin into the prepared solution was commenced.

E. Spraying Procedure:

P22-27.5 (1.48 g), Rifampin (0.26 g) and Minocycline (0.26 g) were weighed into a 250 mL of amber jar. 180 mL of dichloromethane and 20 mL of methanol were added and then dissolved using a magnetic stirrer. 50 mL of solution were drawn into an airtight syringe which was connected to a Sonotek sprayer. The syringe was placed on a syringe pump which had a designated pushing speed. Then the pin was inserted into the 200 [µL pipette tip as described above, and the pipette was affixed to a mechanical stirrer. When the stirrer started to rotate, the sprayer was started and the syringe pump to coat the pin.

F. Coating Polyethylene by Casting and Curing at 70° C.

Weigh P22-27.5 (0.85 g) and PEG 1000 (0.15 g) were weighed into a 20 mL clean amber vial. 9 mL of dichloromethane and 1 mL methanol were added and shaken to dissolve using a vortex shaker. The solution was poured onto a leveled TEFLON coated glass sheet. The wet film was covered and allowed to dry under ambient conditions. After the film was dry, it was transferred onto the polyethylene sheet that is to be coated. The film was cured at 70° C. under vacuum until the required residual solvent level was obtained.

Similar methods could be used to formulate coatings comprising various amounts and types of polyphenolic polymers, PEGs and drugs. Curing is also possible at other temperatures, including at bout 40° C.

G. Coating Orthopedic Pins

Stainless-steel orthopedic pins were coated as described above with P(22-27.5), P(22-27.5) and 10% PEG-1000 by weight, or P(22-27.5) and 10% Pluronic L44 by weight. FIG. 1 shows an uncoated pin and the three coated pins.

II. Properties

A. Sterilization

Figure 2:
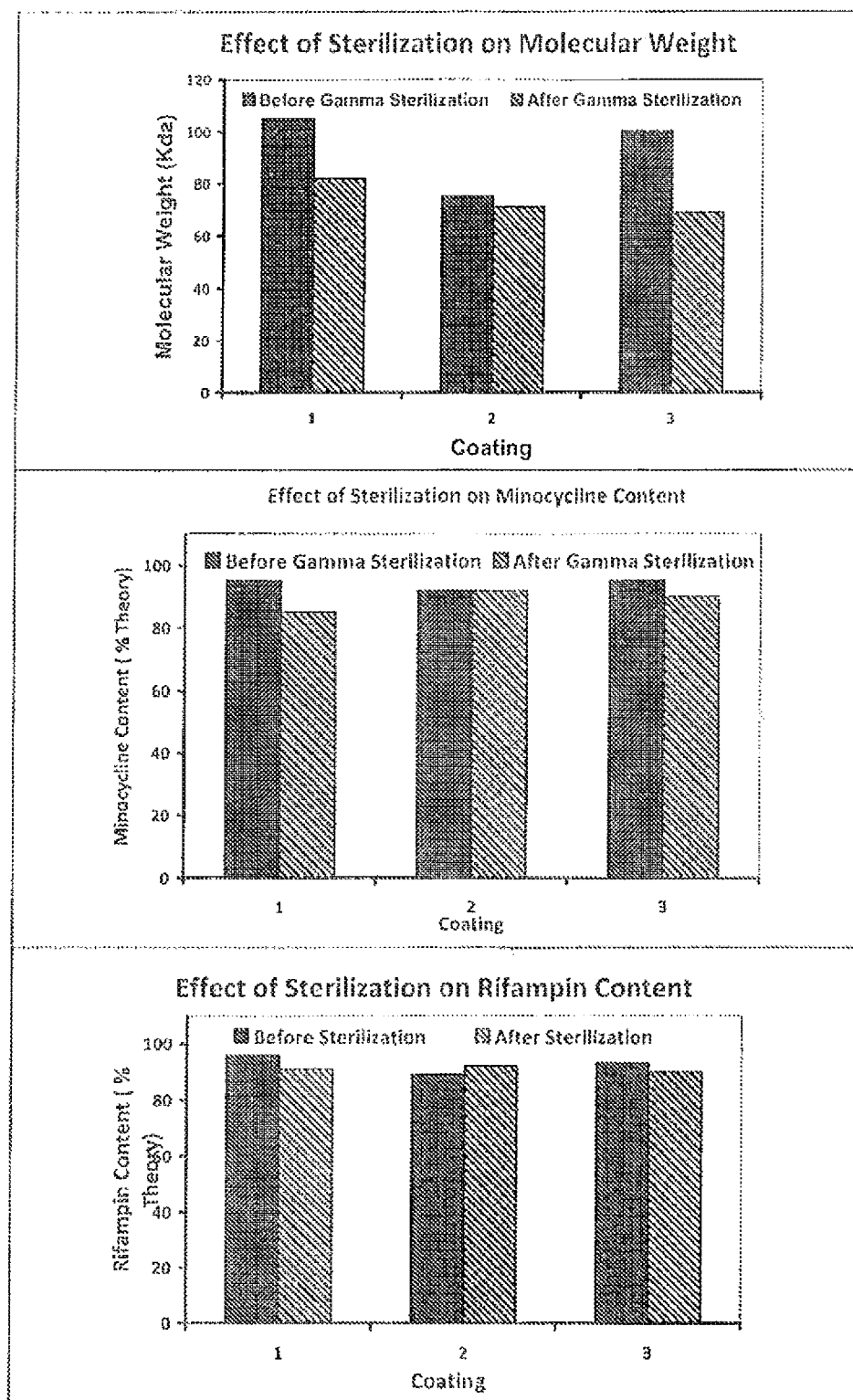
FIG. 2 shows the effect of sterilization on the molecular weight and drug content of the coating.

Medical devices coated with P(22-27.5), 10% PEG-1000 by weight, or P(22-27.5):10% Pluronic L44 blend were sterilized with gamma irradiation. FIG. 2 shows that the sterilization had a minimal effect on the coating as measured by molecular weight and drug content.

B. Release of Minocycline and Rifampin from Coated Pins

Figure 3:
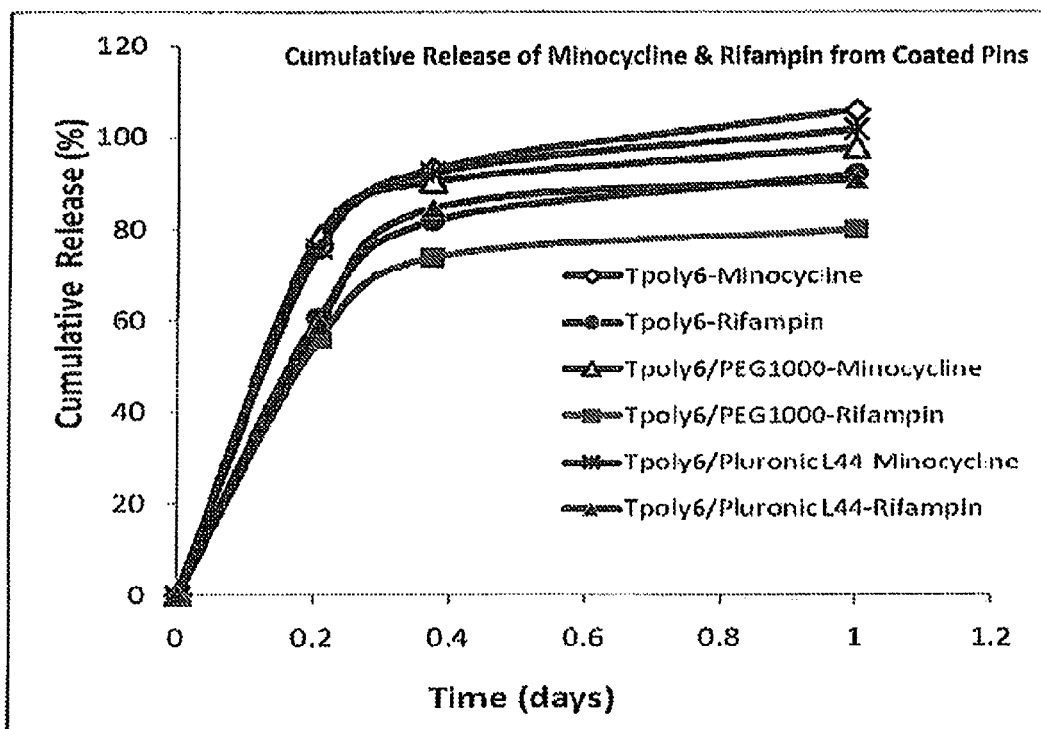
FIG. 3 shows the cumulative release of minocycline or rifampin from the coated pins as a function of time.
Figure 4:
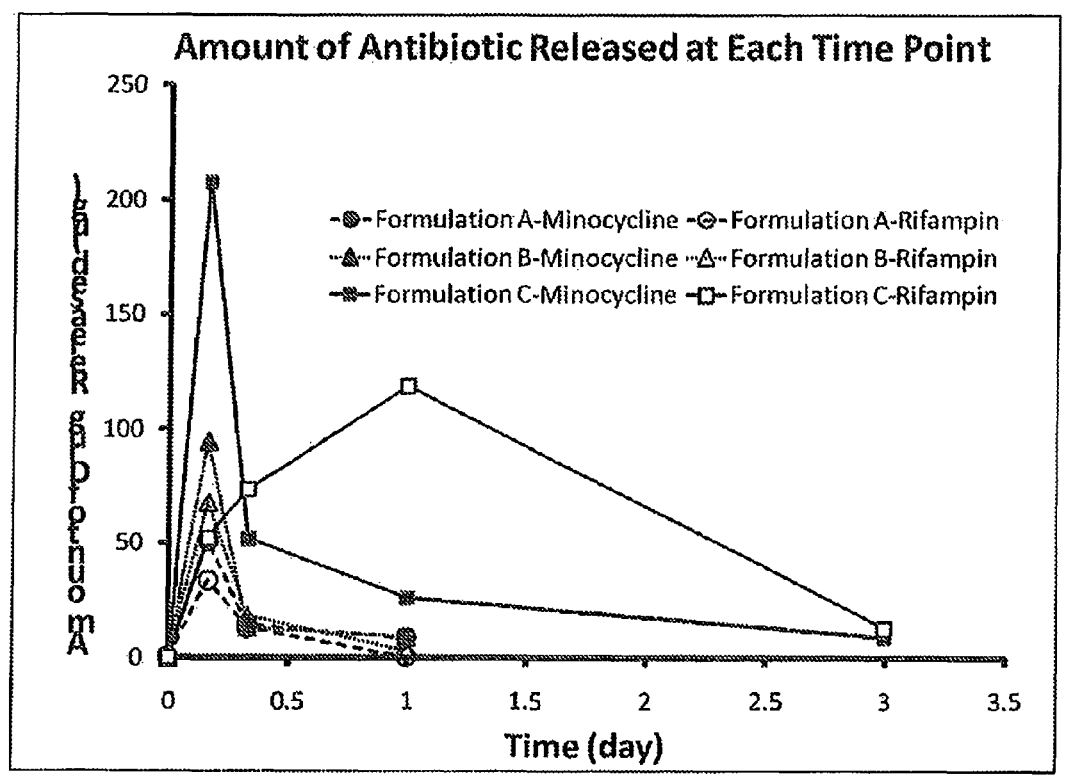
FIG. 4 shows the amount of antibiotic released at each time point.

Orthopedic pins coated with P(22-27.5), P(22-27.5):10% PEG-1000 by weight, or P(22-27.5):10% Pluronic L44 in combination with minocyclin or rifampin were prepared as described above. The pins were placed in PBS at 37° C. and a sample withdrawn periodically for determination of minocyclin or rifampin content by HPLC. FIG. 3 shows the cumulative release of minocyclin or rifampin into PBS from the coated pins as a function of time. FIG. 4 shows the amount of antibiotic released at each time point.

C. Zone of Inhibition Studies

The ZOI for antibiotic coated meshes was determined according-to the Kirby-Bauer method. *Staphylococcus epidermidis* or *Staphylococcus aureus* were inoculated into Triplicate Soy Broth (TSB) from a stock culture and incubated at 37° C. until the turbidity reached McFarland #0.5 standard (1-2 hours). Plates were prepared by streaking the bacteria onto on Mueller-Hinton II agar (MHA) three times, each time swabbing the plate from left to right to cover the entire plate and rotating the plate between swabbing to change direction of the streaks.

A pre-cut piece (1-2 cm$^2$) of spray-coated mesh was firmly pressed into the center of pre-warmed Mueller Hinton II agar plates and incubated at 37° C. Pieces were transferred every 24 h to fresh, pre-warmed Mueller Hinton II agar plates using sterile forceps. The distance from the sample to the outer edge of the inhibition zone was measured every 24 h and is reported on the bottom row in Table 2 and 3 for each sample. The top row for each sample represents difference between the diameter of the ZOI and the diagonal of the mesh. Table 2 shows the ZOI results for meshes placed on *S. epidermidis* lawns and Table 3 shows the ZOI results for meshes placed on *S. aureus* lawns. Additionally, three pieces were removed every 24 h for analysis of residual minocycline and rifampin.

Figure 5:
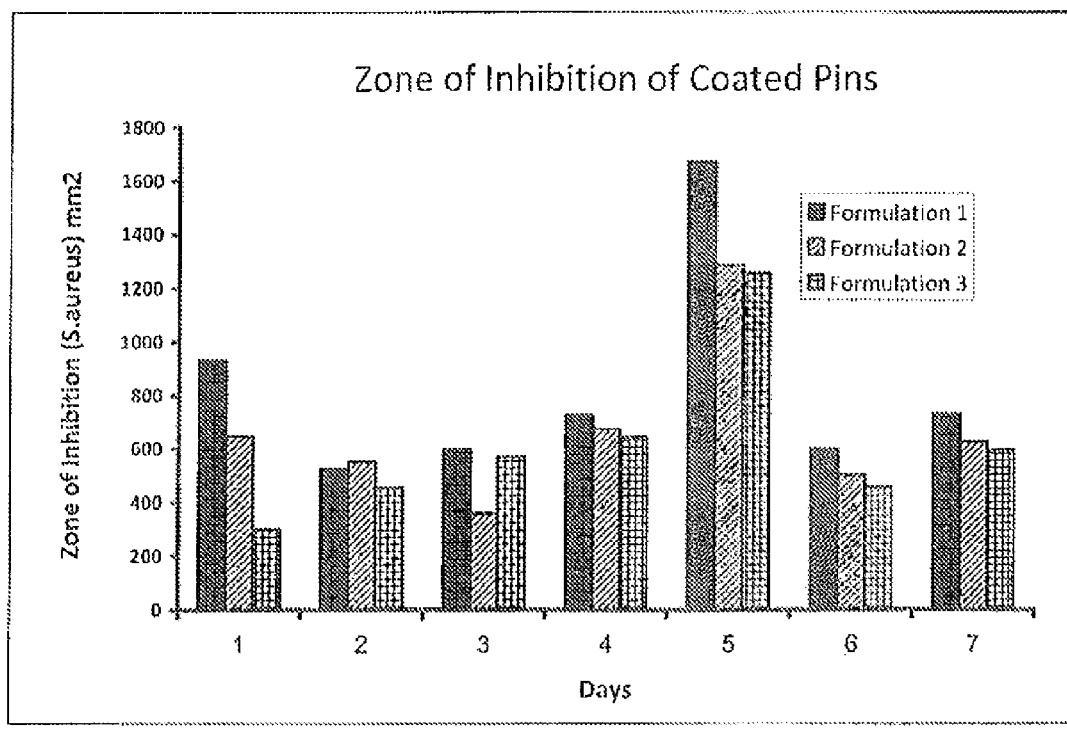
FIG. 5 shows the zone of inhibition ("ZOI") for various coated substrates.

FIG. 5 shows the total ZOI on *S. aureus* for meshes with coated with P (22-27.5), P (22-27.5):10% PEG-1000 by weight, or P(22-27.5):10% Pluronic L44 in combination with minocyclin or rifampin.

D. P(DTE Succinate) with Varying Percentages of Free Carboxylate

Devices of titanium, stainless steal, ultra-high-molecular-weight polyethylene and very-high-molecular-weight polyethylene were coated with P-22 (p(DTE succinate)), P22-10 (p(DTE co 10% DT succinate)), or P22-15 (p(DTE co 10% DT succinate)) blended with 10% of PEG-400, PEG-400-Acid, PEG-1000, PEG-3350 and Pluronic L44 as described above.

Figure 6:
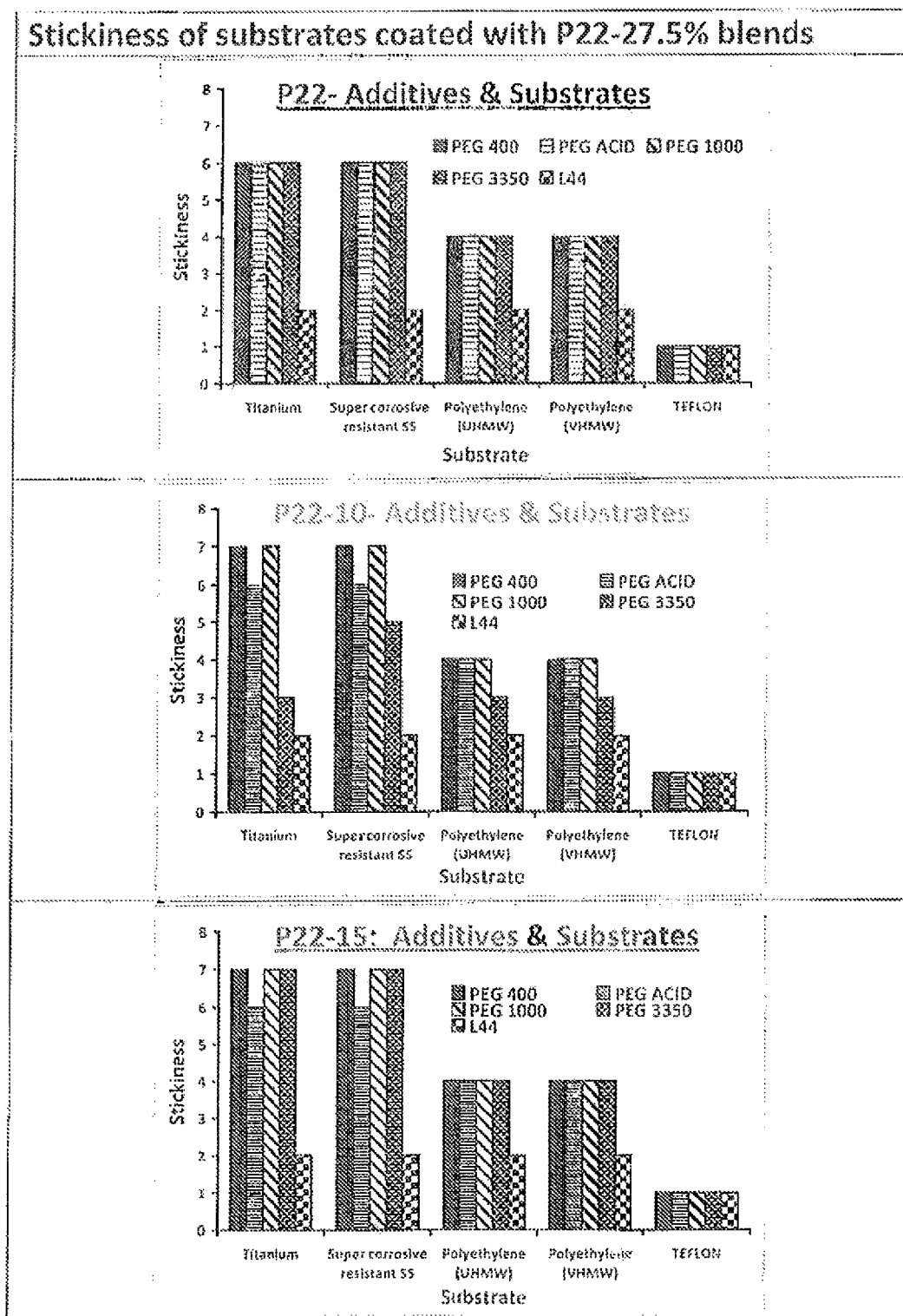
FIG. 6 shows the 'stickiness' of substrates coated with P22-27.5% blended with 10% of PEG-400, PEG-Acid, PEG-1000, or PEG-3350 as compared to Teflon.

FIG. 6 shows the 'stickiness' of the coated substrate as compared to Teflon. According to the data, there is at least about a 6-fold increase in stickiness for metal substrates and about a 4-fold increase for polyethylene substrates.

E. P(DTH Adipate)

Devices of titanium, stainless steal, ultra-high-molecular-weight polyethylene and very-high-molecular-weight polyethylene were coated with P64 (p(DTH adipate)) or P(DThexyl adipate)) blended with 10% of PEG-400, PEG-Acid, PEG-1000, or PEG 3350 as described above.

Figure 7A:
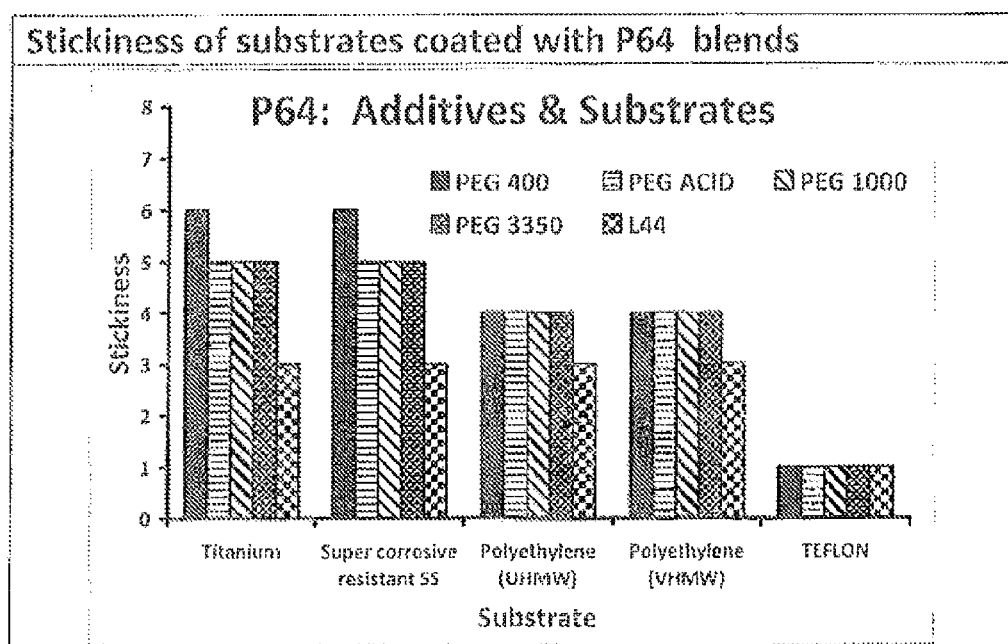
FIGS. 7A and 7B shows the 'stickiness' of substrates coated with P1012 blended with 10% of PEG-400, PEG-Acid, PEG-1000, or PEG-3350 as compared to Teflon.

FIG. 7a shows the 'stickiness' of the coated substrate as compared to Teflon. According to the data, there is about a 3-6-fold increase in stickiness for metal substrates and about a 3- to 4-fold increase for polyethylene substrates.

F. P (DTdodecyl dodecanoate)

Devices of titanium, stainless steal, ultra-high-molecular-weight polyethylene and very-high-molecular-weight polyethylene were coated with P1012 (p(DTD DD) or p(DTdodecyl dodecanoate)) blended with 10% of PEG-400, PEG-Acid, PEG-1000, or PEG 3350 as described above.

Figure 7B:
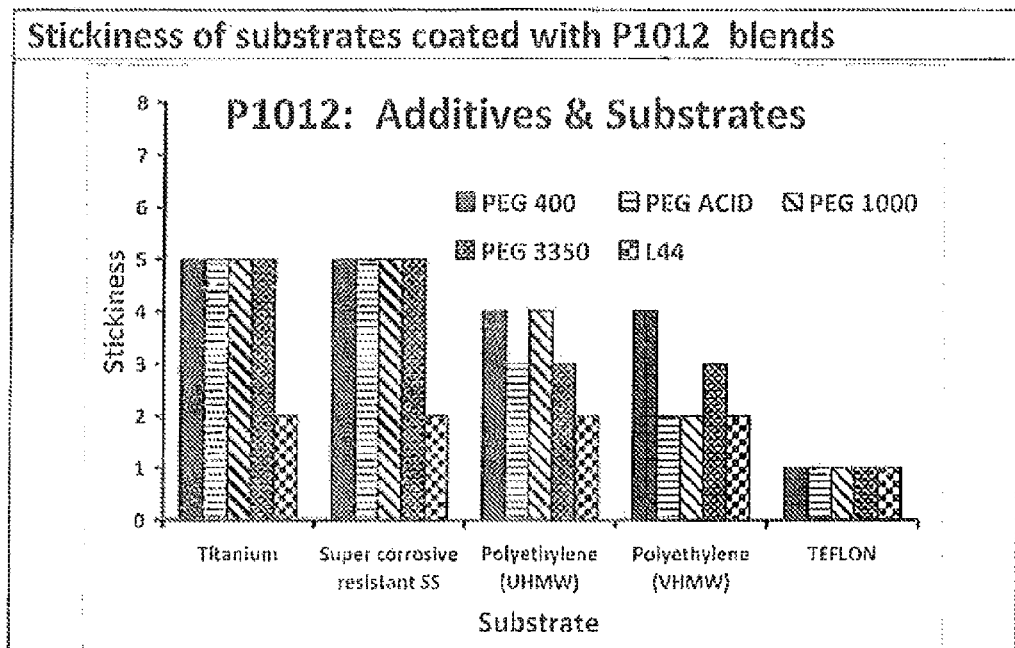

FIG. 7b shows the 'stickiness' of the coated substrate as compared to Teflon. According to the data, there is about a 5-fold increase in stickiness for metal substrates and about a 2- to 4-fold increase for polyethylene substrates. This shows that even a polymer with a lower surface energy, such as p1012, shows an increase in the stickiness even on a low energy surface such as the polyethylenes.

G. P(DTPP Glutarate), P(MeDHB-15 DHB Glutarate), and P(TE-DG-TE-Glutarate) Coatings Devices of titanium, stainless steal, ultra-high-molecular-weight polyethylene and very-high-molecular-weight polyethylene were coated with p(DTPP Glutarate), p(MeDHB-15 DHB Glutarate), or p(TE-DG-TE-Glutarate) blended with 10% of PEG-400, PEG-Acid, PEG-1000, or PEG-3350 as described above.

Figure 8:
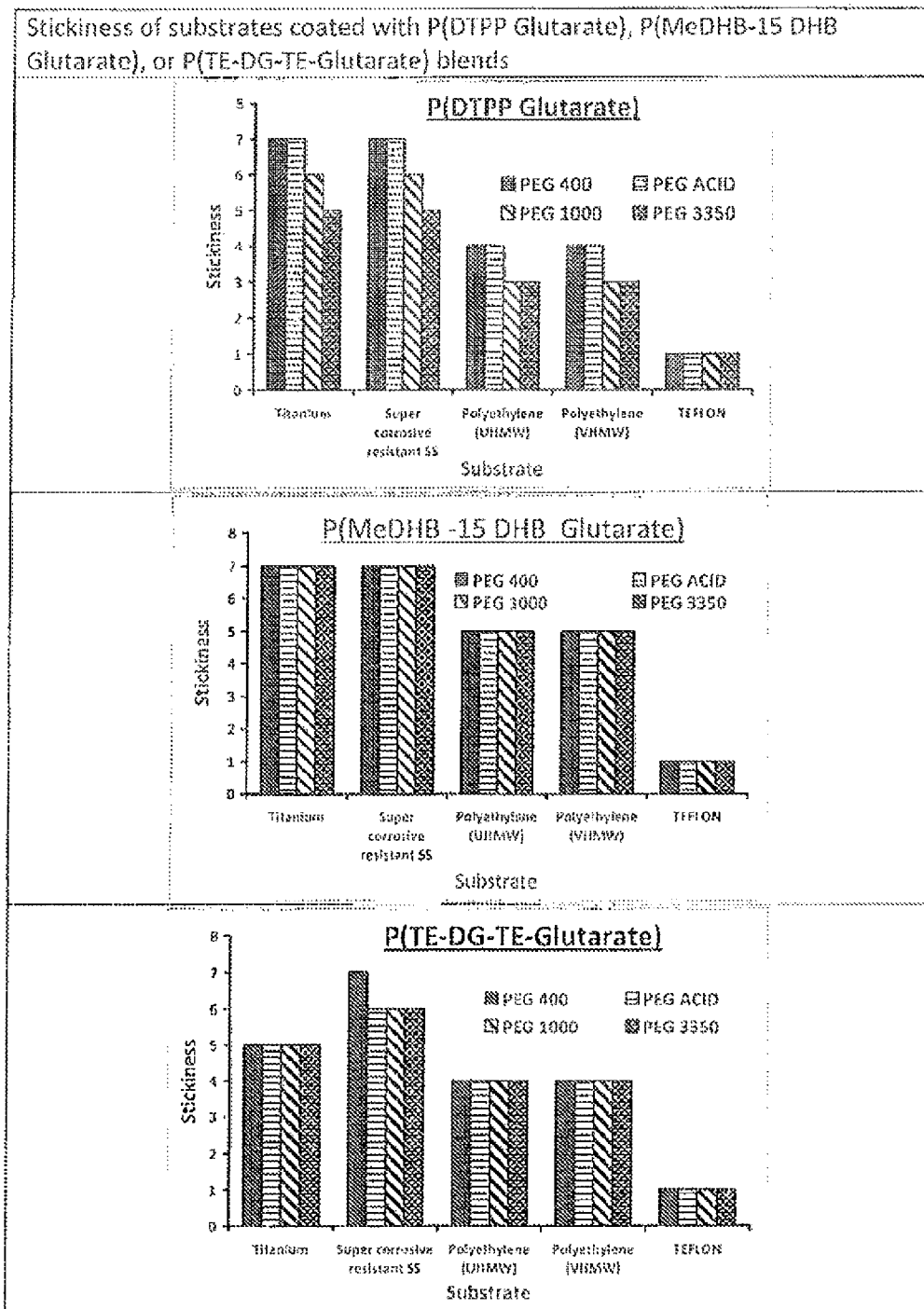
FIG. 8 shows the 'stickiness' of substrates coated with P(DTPP Glutarate), P(MeDHB-15 DHB Glutarate), or P(TE-DG-TE-Glutarate) blended with 10% of PEG-400, PEG-Acid, PEG-1000, or PEG-3350 as compared to Teflon.

FIG. 8 shows the 'stickiness' of the coated substrate as compared to Teflon. According to the data, there is about a 5- to 7-fold increase in stickiness for metal substrates and about a 3- to 4-fold increase for polyethylene substrates.

III. Implantation of a Coated Orthopedic Pin

*S. aureus* Bioluminescent Strain

The bioluminescent *S. aureus* SH1000 strain, ALC2906, which contained the shuttle plasmid pSK236 with the penicillin-binding protein 2 (pbp2) promoter fused to the luxABCDE reporter cassette from *Photorhabdus lumninescens*, was used in all experiments. This *S. aureus* strain naturally emitted bioluminescent signals from live, actively metabolizing bacteria in all stages of the *S. aureus* life cycle.

Preparation of *S. aureus* for Inoculation into the Joint Space

*S. aureus* bioluminescent strain ALC2906 has a chloramphenicol resistance selection marker and chloramphenicol (10 sg/ml; Sigma-Aldrich) was supplemented to all cultures. *S. aureus* was streaked onto tryptic soy agar plates (tryptic soy broth [TSB] plus 1.5% bacto agar [BD Biosciences]) and grown at 37° C. overnight. Single colonies of *S. aureus* were cultured in TSB and grown overnight at 37° C. in a shaking incubator (240 rpm) (MaxQ 4450; Thermo). Mid-logarithmic phase bacteria were obtained after a 2 h sub-culture of a 1150 dilution of the overnight culture. Bacterial cells were pelleted, resuspended and washed 3× in PBS. Bacterial concentrations were estimated by measuring the absorbance at 600 nm (A6oo; Biomate 3 [Thermo]). Colony forming units were verified after overnight culture of plates.

Mice 12-week old male C57BL/6 wildtype mice were used (Jackson Laboratories). In some experiments, 12-week old male LysEGFP mice, a genetically engineered mouse line on a C57BL/6 background possessing green-fluorescent myeloid cells (mostly neutrophils) as a consequence of 'knockin' of enhanced green fluorescent protein (EGFP) into the lysozyme M gene, were used.

Mouse Surgical Procedures

Mice were anesthetized via inhalation isoflurane (2%). The surgical procedure was modified from previous work. A skin incision was made over the right knee (FIG. 9A). The distal right femur was accessed through a medial parapatel-lar arthrotomy with lateral displacement of the quadriceps-patellar complex (FIG. 9B). After locating the femoral intercondylar notch (FIG. 9B), the femoral intramedullary canal was manually reamed with a 25 gauge needle (FIG. 9C). An orthopaedic-grade stainless steel Kirschner (K)-wire (diameter 0.6 mm) (Synthes) was surgically placed in a retrograde fashion and cut with 1 mm protruding into the joint space (FIG. 9D). An inoculum of *S. aureus* in 2 μl of normal saline was pipetted into the joint space containing the cut end of the implant (FIG. 9E). The quadriceps-patellar complex was reduced to the midline (FIG. 9F) and the surgical site was closed with Dexon 5-0 sutures (FIG. 9G). A representative radiograph demonstrates the position of the implant with good intramedually fixation of the stem and prominence of the cut surface in the joint (FIG. 9H). Buprenorphine (0.1 mg/kg) was administered subcutane-ously every 12 hours as an analgesic for the duration of the experiment.

Quantification of In Vivo *S. aureus* (In Vivo Biolumines-cence Imaging and Colony Forming Units [CFUs])

Mice were anesthetized via inhalation of isoflurane (2%) and in vivo bioluminescence imaging was performed by using the Xenogen in vivo imaging system (Xenogen IVIS®; Caliper Life Sciences). Data are presented on color scale overlaid on a grayscale photograph of mice and quantified as maximum flux (photons per second (s) per cm per steradian (sr) [p/s/cm/sr]) within a circular region of interest ($1 \times 10^3$ pixels) by using Living Image® software (Xenogen). To confirm that the bioluminescence signals corresponded to the bacterial burden in vivo, bacteria adher-ent to the implants were quantified by detaching the bacteria from the implant by sonication in 1 ml 0.3% Tween-80 in TSB for 10 minutes followed by vortexing for 5 minutes as previously described. In addition, bacteria in the joint tissue were confii toed by homogenizing bone and joint tissue (Pro200® Series homogenizer; Pro Scientific). The number of bacterial CFUs that were adherent to the implant and in the joint tissue was determined by counting CFUs after overnight culture of plates and was expressed as total CPUs harvested from the implant and joint tissue.

Quantification of Neutrophil Recruitment to the Infected Post-Operative Joint (In Vivo Fluorescence Imaging)

To obtain a measurement of neutrophil infiltration, LysEGFP mice were used. After in vivo bioluminescence imaging, in vivo fluorescence imaging was performed by using the Xenogen IVIS® (Caliper Life Sciences). EGFP-expressing neutrophils within the post-operative site were visualized by using the GFP filter for excitation (445-490 nm) and emission (515-575 nm) at an exposure time of 0.5 seconds. Data are presented on color scale overlaid on a grayscale photograph of mice and quantified as total flux (photons/s) within a circular region of interest ($1 \times 10^3$ pixels) by using Living Image® software (Xenogen).

Histologic Analysis

Mice were euthanized via inhalation carbon dioxide and joint specimens were fixed in formalin (10%) overnight. Specimens were decalcified by incubation in Decalcifier II® solution (Surgipath) for 6 h and specimens were processed and embedded in paraffin. Sagittal sections of 4 μm thick-ness were cut and then were stained with hematoxylin and eosin (H&E) and Gram stain.

Variable-pressure Scanning Electron Microscopy

A field emission variable pressure scanning electron microscope (FE-SEM Zeiss Supra VP40) was used to obtain a digital image of the cut end of the implants. Conductive graphite glue was used to position the pins on a graphite stub. Pressure in the microscope chamber was maintained at 25 Pa, which allowed the examination of the implant surface without the need of sputter coating. Secondary and in-lens detectors were used to reveal the topographical characteris-tics of the surface. Examination of the implant occurred at regular intervals by tilting the pin between −4 and 10 degrees and rotating it every 30 degrees for a total of 360 degrees.

Coating of Metallic Implants with an Antibiotic-impreg-nated Bioresorbable Polymer A bioresorbable polymer impregnated with rifampin and minocycline was used. To coat the stainless steel K-wire implants with this antibiotic-impregnated polymer, K-wires were hand-dipped in a mixture of bioresorbable tyrosine-derived polyesteramide (P22-27.5), PEG400, rifampin and minocycline and methylene chloride as described in Example I. Vehicle coating consisted of bioresorbable tyro-sine-derived polyesteramide, PEG400 and methylene chlo-ride only (no antibiotic). The coated pins were heat dried for at least 12 h until residual solvent was less than 600 ppm, stored at −15° C. and sterilized by gamma irradiation. Three different formulations were generated (Coatings A, B and C) with the following approximate antibiotic concentrations: Coating A: 32.5 μg/mm$^3$ of rifampin and 36.1 μg/mm$^3$ of minocycline; Coating B: 46.1 μg/mm$^3$ of rifampin and 47.7 μg/mm$^3$ of minocycline; and Coating C: 97.4 μg/mm$^3$ of rifampin and 104.2 μg/mm$^3$ of minocycline. The coatings were repeatedly dipped until the thickness of Coating A and Coating B were ~40-45 μm whereas and Coating C was ~80-90 μm. Thus, Coatings A and B would elute at the same rate whereas Coating C would elute slower because it had double the coating thickness.

Statistical Analysis

Data were compared by using a Student's t-test (two-tailed). All data are expressed as mean±standard error of the mean (sem) where indicated. Values of p<0.05, p<0.01 and p<0.001 were considered statistically significant.

In Vivo Bioluminescence Imaging to Measure the Bacte-rial Burden in Real-Time

Figure 9:
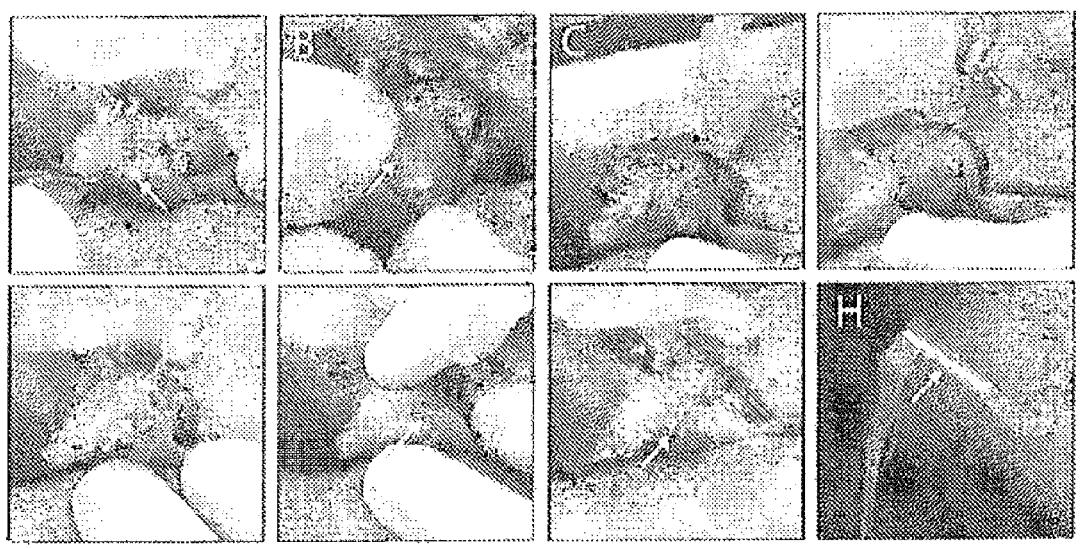
FIG. 9 shows a mouse surgical procedure where an implant is inserted into a joint space.

To model a post-arthroplasty infection, a orthopaedic-grade K-wire (Synthes, Inc., West Chester, Pa.) was surgi-cally placed into the femur with the cut end protruding into knee joint and an inoculum of *S. aureus* was pipetted into the joint space before closure (FIG. 9). To measure the bacterial burden within the infected post-operative joints in real-time, we used a bioluminescent *S. aureus* strain (SH1000) that naturally emits lights from live, ATP-producing bacteria at all stages of the *S. aureus* life cycle. The bacterial burden was subsequently measured on post-operative days 0, 1, 3, 5, 7 and 10 in anesthetized mice in real-time by using the Xenogen in vivo imaging system (Xenogen IVIS®; Caliper Life Sciences).

Figure 10A:
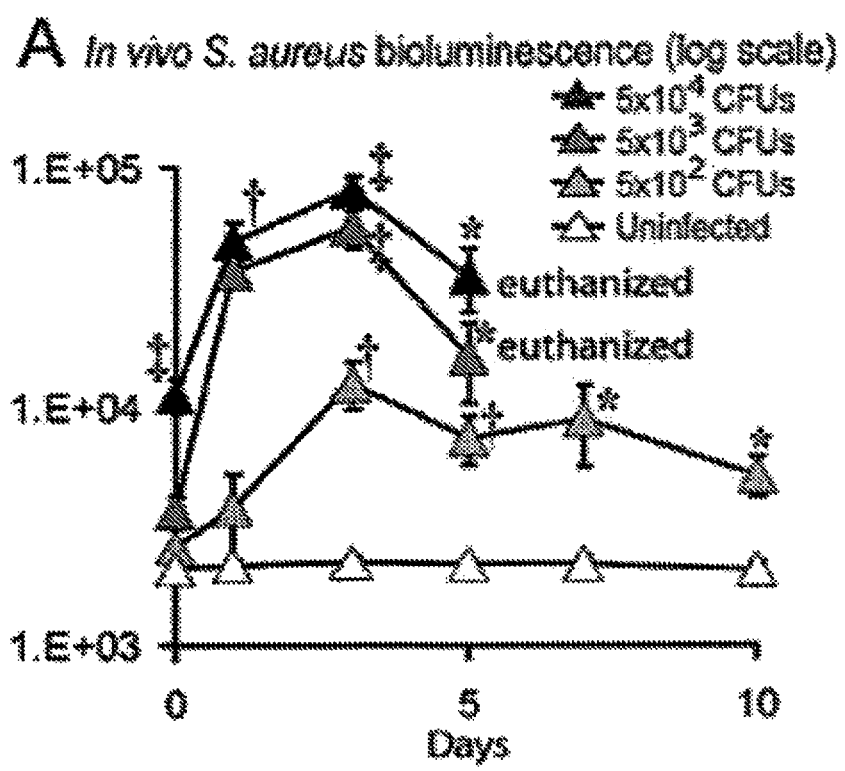
FIG. 10A shows in vivo *S. aureus* bioluminescence.
Figure 10B:
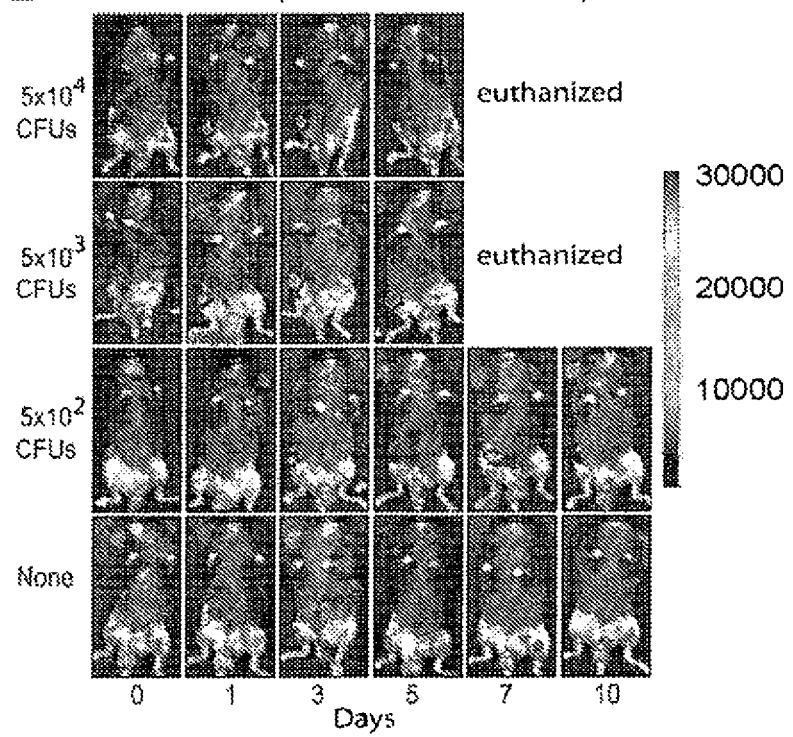
FIG. 10B shows Bacterial Counts (in vivo bioluminescence).

To determine the optimal bacterial inoculum to produce a chronic implant infection, C57BL/6 mice were inoculated with increasing logarithmic concentrations of *S. aureus* ($5\times10^2$, $5\times10^3$ and $5\times10^4$ CFUs/2 µl). During the first 5 days after the inoculation, mice that received $5\times10^3$ or $5\times10^4$ CFUs had 20- to 50-fold higher bioluminescence signals than uninfected mice (FIG. 10A, B). Clinically, both of these groups of mice developed marked inflammation as characterized by increased swelling and decreased mobility of the affected leg and were euthanized on post-operative day 5. Thus, inocula of $5\times10^3$ or $5\times10^4$ CFUs of *S. aureus* induced markedly high bioluminescent signals and produced clinical signs of infection that was consistent with an acute purulent joint infection. In contrast, mice that received an inoculum of $5\times10^2$ CFUs developed signs of infection in the affected leg that were only minimally different than uninfected mice. These mice had up to 6- to 8-fold higher bioluminescence signals than the background levels of uninfected control mice at all post-operative days through day 10 (FIG. 10A, B). The mild clinical findings combined with the low level of bacterial bioluminescence allowed us to follow the infection in the mice that received the inoculum of $5\times10^2$ CFUs for at least 10 days, which more closely resembled a chronic and persistent infection. Thus, the inoculum of $5\times10^2$ CFUs was used in all subsequent experiments.

Figure 10C:
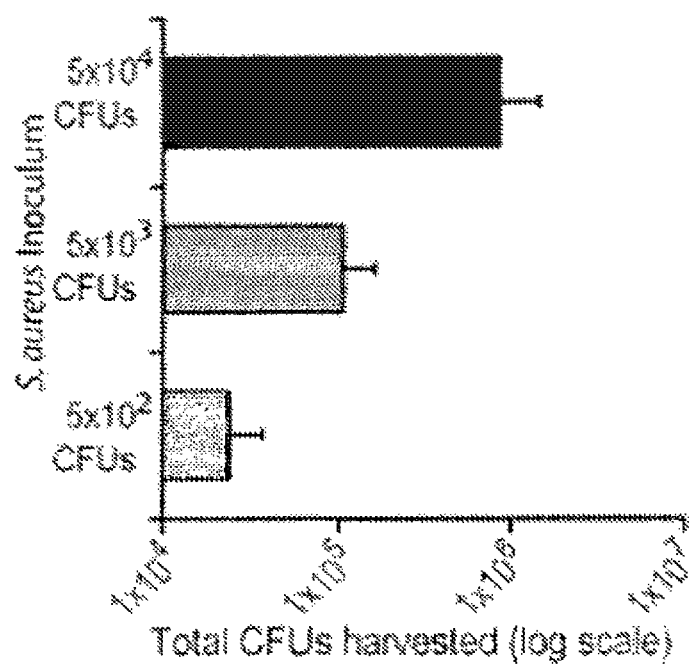
FIG. 10C shows Total *S. aureus* CFUs harvested from the implant and joint tissue on Day 5.
Figure 10D:
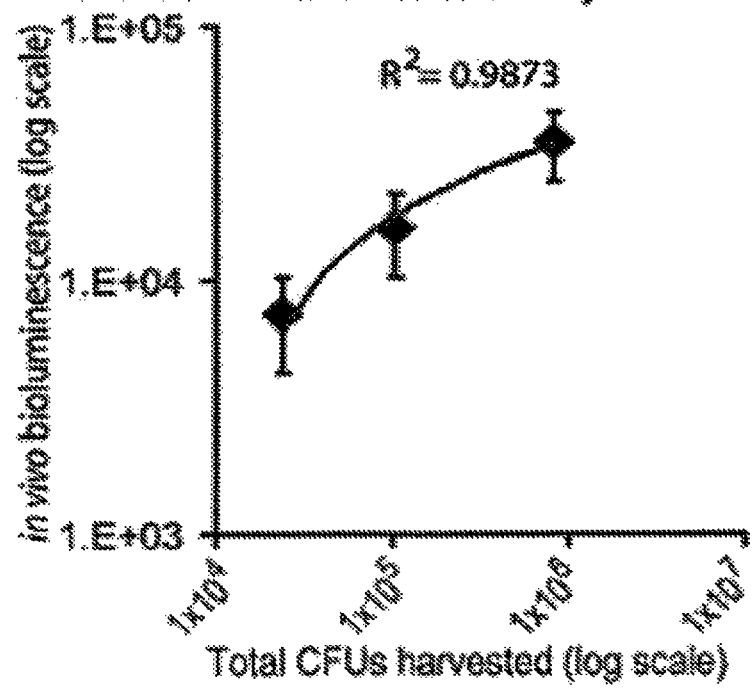
FIG. 10D shows Correlation of in vivo bioluminescence and total CFUs harvested on Day 5.
Figure 11A:
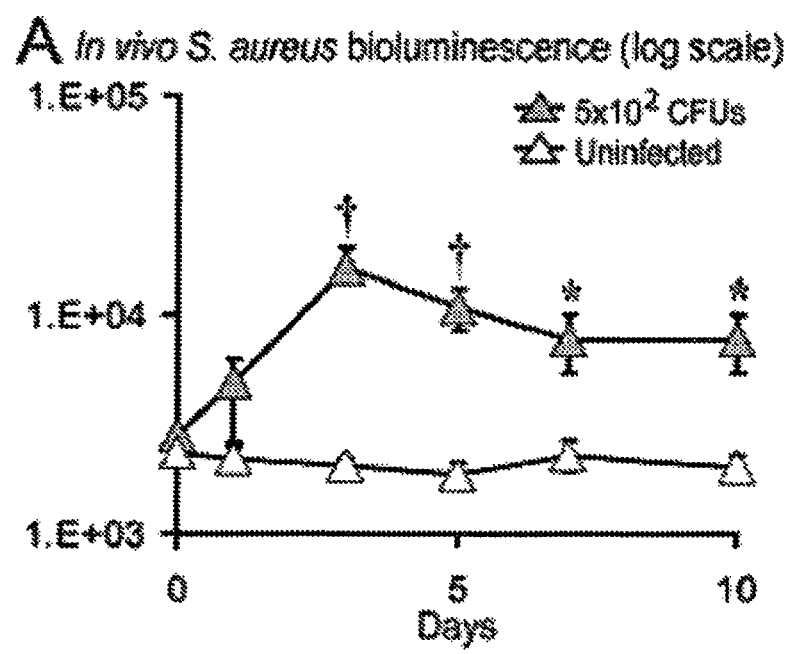
FIG. 11A shows in vivo *S. aureus* bioluminescence.
Figure 11B:
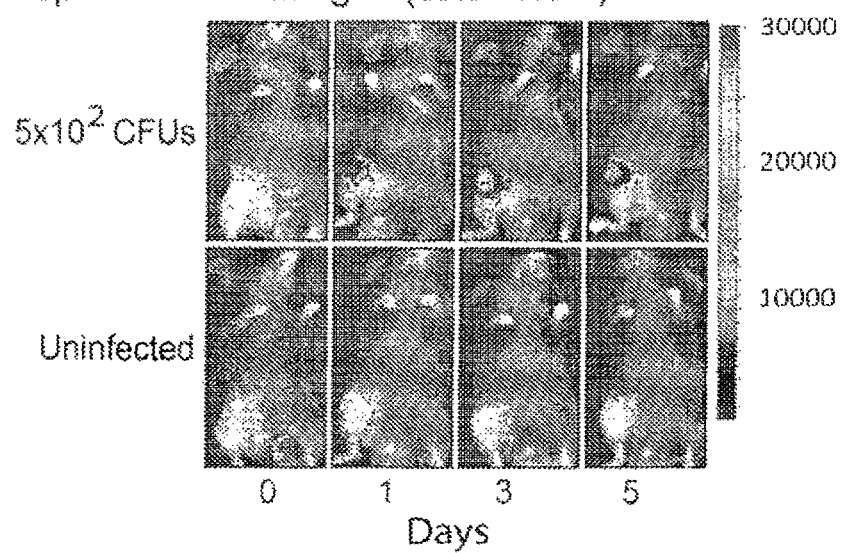
FIG. 11B shows in vivo *S. aureus* bioluminescence representative images.
Figure 11C:
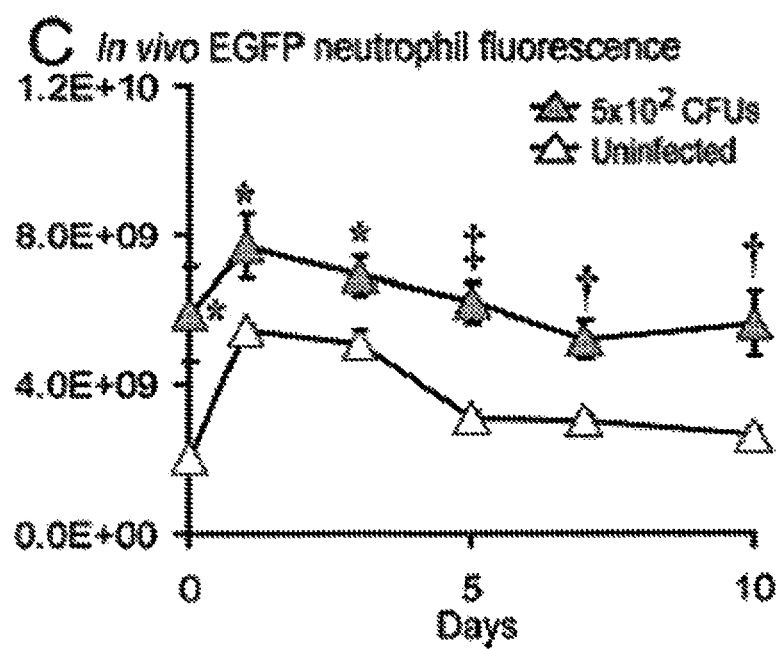
FIG. 11C shows in vivo EGFP neutrophil fluorescence.
Figure 11D:
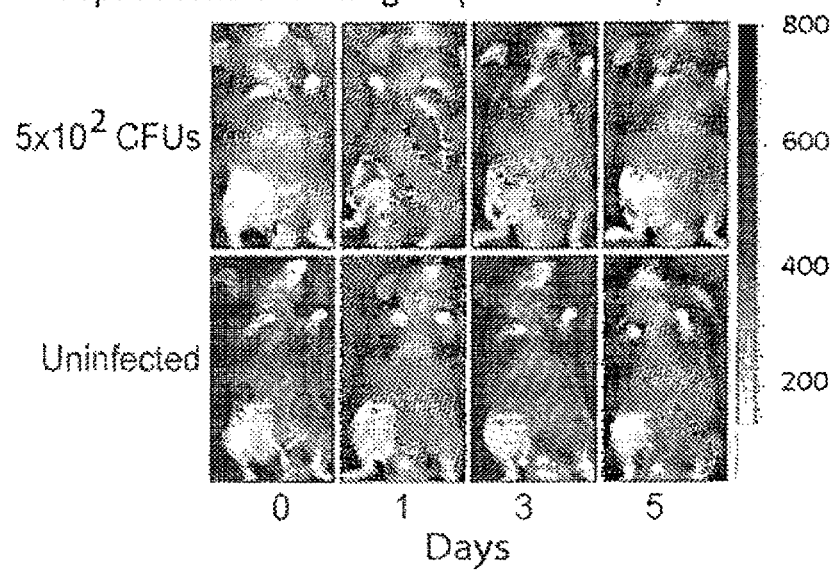
FIG. 11D shows in vivo EGFP neutrophil fluorescence representative images.

To confirm that the in vivo bioluminescence signals accurately represented the bacterial burden in vivo, traditional bacterial counts were performed on post-operative day 5 from bacteria adherent to the implant and present in the joint tissue (FIG. 10C). Mice that were inoculated with $5\times10^4$, $5\times10^3$ and $5\times10^5$ CFUs had a total bacterial burden ex vivo of $8.3\times14^5$, $1\times10^5$ and $2.4\times10^4$ CFUs, respectively (FIG. 10C). In addition, the in vivo bioluminescent signals correlated with the corresponding ex vivo bacterial CFUs (correlation coefficient of determination: $R^2$ 0.9873; FIG. 10D), suggesting that the in vivo bioluminescence signals at least through day 5 provided an approximation of the actual bacterial burden in vivo. However, since the bacterial strain used had the lux genes in a plasmid that is maintained in vitro under chloramphenicol selection, the plasmid is likely lost during the in vivo infection over time. In broth culture without selection, the plasmid was stable for the first 3 days in vitro with greater than 97% of bacteria still containing the plasmid whereas only 53%, 38% and 21% of the bacteria still contained the plasmid on days 5, 7 and 10, respectively (data not shown). Thus, although the bioluminescent signals obtained with this strain provide an approximation of the bacterial burden in vivo, it is likely an underestimate of the actual bacterial burden, especially at later time points.

In Vivo Fluorescence Imaging to Measure Neutrophil Infiltration in Real-Time

The degree of inflammation within the post-operative knee joints was measured by quantifying neutrophil infiltration, a key correlate for inflammation and infection. This was accomplished by using in vivo fluorescence imaging of LysEGFP mice, a genetically engineered mouse strain that possesses green-fluorescent neutrophils. The bioluminesce nt *S. aureus* strain infected into the knee joints of LysEGFP mice enabled simultaneous measu.

ement of both bacterial burden and neutrophil infiltration on post-operative days 0, 1, 3, 5, 7 and 10 (FIG. 11). Similar to C57B/16 mice in FIG. 2, *S. aureus* ($5\times10^2$ CFUs)-infected LysEGFP mice developed bioluminescence signals that were up to 8-fold higher than the background levels of uninfected control mice through day 10 (FIG. 11A). In addition, the *S. aureus*-infected LysEGFP mice had 20-40% higher EGFP-neutrophil fluorescent signals than uninfected control mice on all post-operative days 1 to 10 (FIG. 11B). This degree of neutrophil recruitment, confirms our clinical observations that the inoculum of $5\times10^2$ CFUs produced a low-grade inflammatory response, suggesting that EGFP-neutrophil fluorescence provides a quantifiable measurement of the clinical inflammation observed in our model.

Histologic Analysis of Post-Operative Knee Joints

Figure 12:
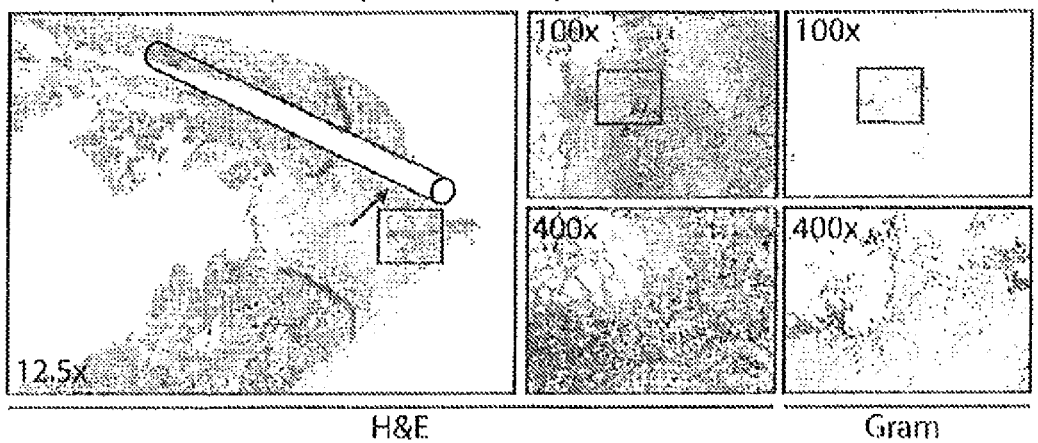
FIG. 12 shows a histologic analysis of post-operative knee joints in both infected and uninfected models.
Figure 12:
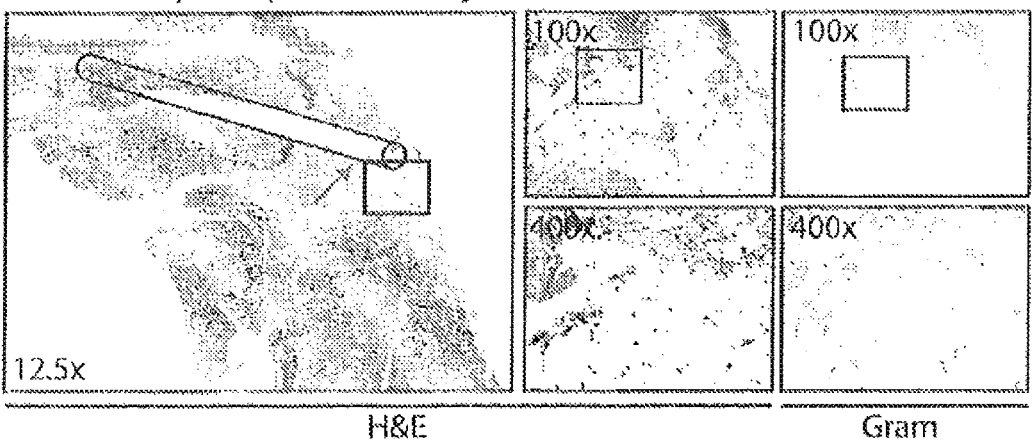

To determine the location of the inflammatory infiltrate and bacterial inoculum within the infected post-operative joints, histologic sections were harvested from *S. aureus*-inoculated ($5\times10^2$ CFUs) and uninfected control mice on post-operative day 1 (FIG. 12). Mice inoculated with *S. aureus* had increased neutrophils in the joint tissue as seen in hematoxylin & eosin (H&E) stained sections. In addition, Gram-positive (blue-staining) bacteria could be readily detected in areas of inflammatory cells. In contrast, uninfected control mice that only had the surgical implant placed had minimal neutrophil infiltration and no bacteria were detected by Gram-stain. These histologic findings corroborate our in vivo bioluminescence and fluorescence imaging data demonstrating that the inoculum of $5\times10^2$ CFUs of *S. aureus* induced neutrophil infiltration and bacterial proliferation in the joint tissue in the area of the implant.

Figure 13:
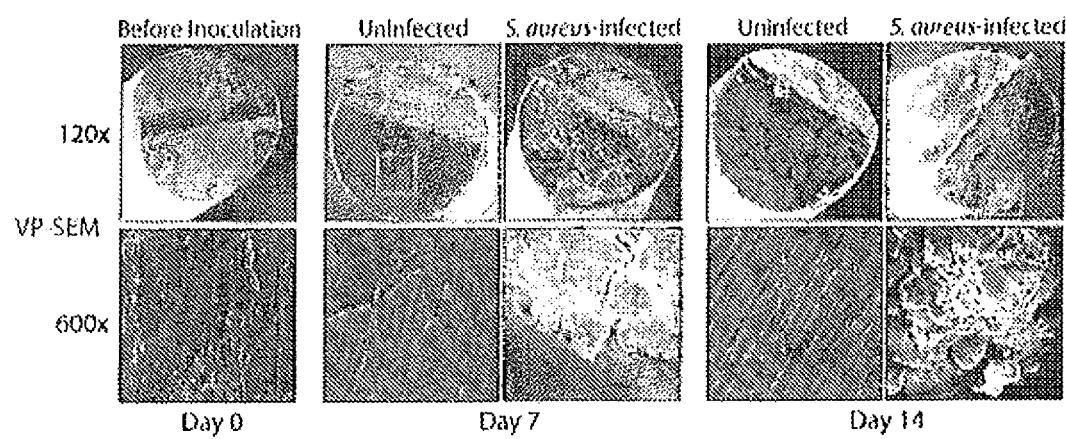
FIG. 13 shows the formation of biofilms on metallic implants in various models.

To evaluate whether biofilm formation occurred on the implants in our mouse model, implants were harvested from euthanized mice on post-operative days 7 and 14 (FIG. 13). To evaluate biofilm formation, we used variable-pressure scanning electron microscopy (VP-SEM), which allows for visualization of biologic samples in their natural state, as there is no need to coat them with a conductive film required for traditional SEM. Thus, VP-SEM enabled the visualization of biofilms on the implants without typical artifacts (dehydration, collapse, distortion, shrinkage, condensation, and aggregation) associated with conventional SEMs that require fixation and sputter coating. Mice inoculated with *S. aureus* had prominent biofilm formation on the cut end of the implants harvested on 7 and 14 post-operative days. In contrast, uninfected mice, which did not have any bacterial inoculation at the time of surgery, had no detectable biofilm formation and the visualized metallic implant surface was virtually identical to implants prior to surgery (Day 0). Thus, the bacteria infected the joint tissue (FIG. 13) and also formed a biofilm on the implant, which is consistent with biofilm formation that occurs in post-arthroplasty infections in patients.

Figure 14:
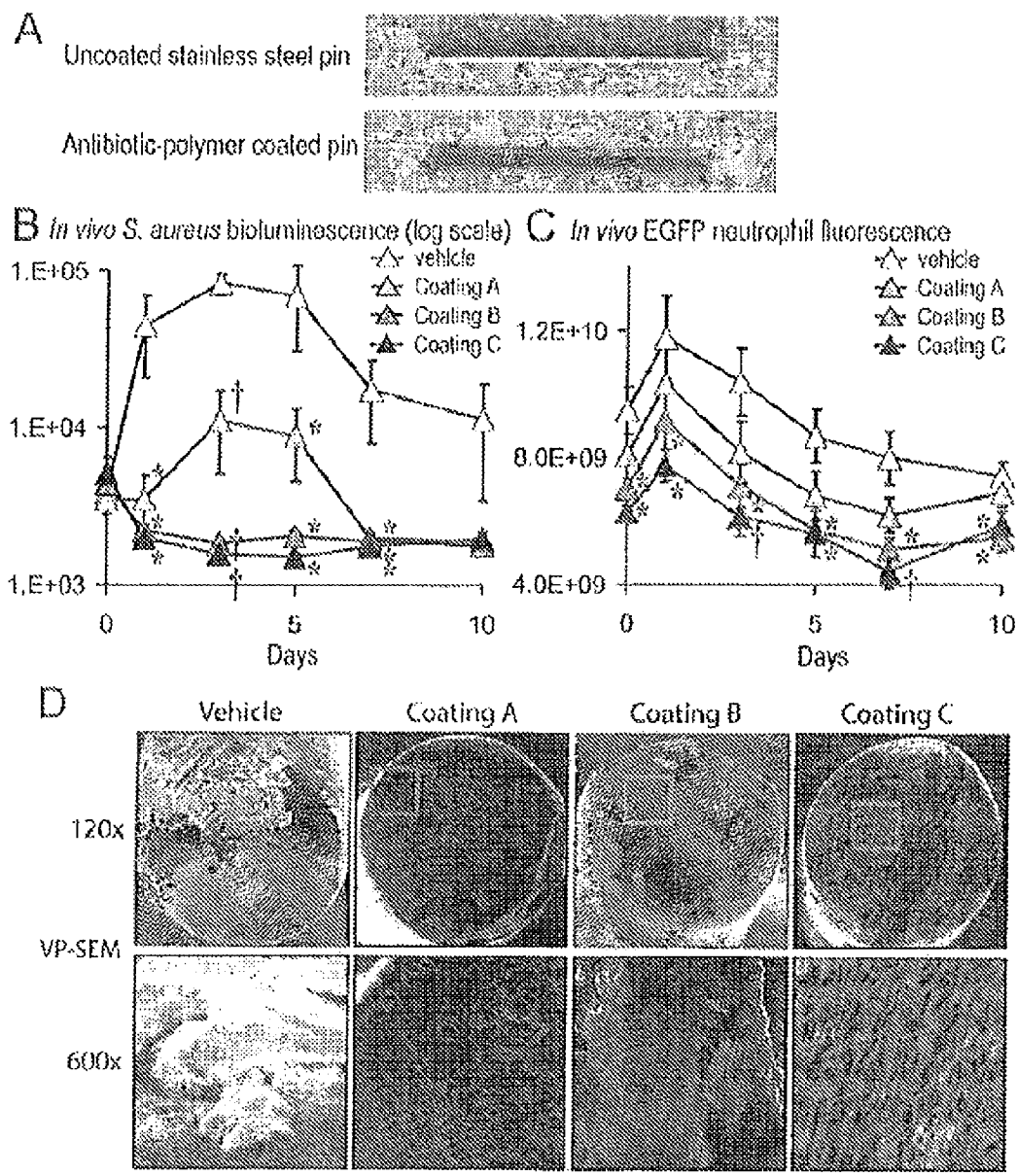
FIG. 14 provides a comparison of bacteria growth when utilizing antibiotic-polymer coated pins and uncoated pins.

A Novel Antibiotic-impregnated Implant Coating to Treat *S. aureus* Post-operative Joint Infection This mouse model was employed to determine the efficacy of a bioresorbable polymer impregnated with rifampin and minocycline in preventing the development of an infection in the joint. Stainless steel K-wires were coated by three coating formulations (Coatings A, B and C), which contained increasing concentrations of the antibiotics, and one vehicle control coating (no antibiotic) (FIG. 14A). In addition, Coatings A and B had the same thickness and would elute the antibiotics at a similar rate whereas Coating C was double the thickness and would elute slower.

These antibiotic-coated implants were surgically placed into the distal femurs of LysEGFP mice and the knee joint space was inoculated with $5.\text{times}.10.\text{sup}.2$ CFUs of *S. aureus*. In vivo imaging was performed on post-operative days 0, 1, 3, 5, 7 and 10 as in FIG. 11. Coatings B and C resulted in bioluminescence signals that were highest at the time of inoculation and were reduced to background levels by day 3 (FIG. 14B). Coating A resulted in bioluminescence signals that were less than the vehicle alone but did increase between 0-3 days before decreasing to background levels by day 7. As expected, the vehicle control coating, which contained no antibiotics, did not inhibit bacterial growth and resulted in bioluminescent signals that were up to 20-fold higher than the initial inoculum and up to 50-fold higher than the two most effective antibiotic-impregnated implant coatings (Coatings B and C). Thus, the antibiotic-impregnated coatings substantially reduced the bacterial burden and prevented infection in post-operative joints as measured by in vivo bioluminescence imaging. Since Coating A resulted in some bacterial growth, whereas no growth was detected with Coatings B or C, it is likely that both the drug concentration and elution rate contributed to the efficacy of these coatings.

The antibiotic-eluting coated implants also substantially reduced clinical signs of inflammation. Mice with Coatings B and C ambulated with notably less guarding of the operative leg than mice with vehicle-coated implants. To obtain a quantifiable measurement of the infection-induced inflammatory response, in vivo fluorescence of EGFP-neutrophils was measured in these LysEGFP mice (FIG. 14C). Coatings B and C, which were most effective in reducing bacterial burden, had EGFP-neutrophil fluorescent signals that were reduced to background levels (i.e. no detectable inflammation) by post-operative day 5. These data demonstrate that antibiotic-impregnated implant coatings markedly reduced the infection-induced neutrophil recruitment and inflammation in a concentration- and elution-dependent fashion.

To determine whether the antibiotic-impregnated implant coatings had any impact on biofilm formation, the implants were harvested from mice on post-operative day 7 and biofilm formation was evaluated by VP-SEM (FIG. 14D). All three antibiotic-impregnated implant coatings (A, B and C) prevented biofilm formation on the cut surface of the pin within the knee joint. In contrast, the vehicle coated pin had readily detectable biofilm formation.

The invention claimed is:

1. A medical device comprising a coating comprising at least one drug, polyethylene glycol and a polyphenolic polymer, the polyphenolic polymer comprising a linear polyesteramide, the coating comprising about 20% to about 70% of the at least one drug, based on a combined weight of the at least one drug, the polyethylene glycol and the polyphenolic polymer, the polyethylene glycol comprising about 3% to about 16% of the combined weight.

2. The medical device of claim 1, wherein the linear polyesteramide comprises monomer units having the formula:

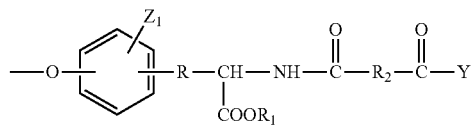

wherein R is $-(CR_3R_4)_a-$ or $-CR_3=CR_4-$;
$R_1$ is selected from the group consisting of hydrogen and a saturated or unsaturated alkyl, aryl, alkylaryl or alkyl ether having from 1 to 20 carbon atoms; or $-(R_5)_qO((CR_3R_4)_rO)_s-R_6$;
$R_2$ is independently selected from the group consisting of a divalent, linear or branched, substituted or unsubstituted alkylene, alkenylene, alkynylene, arylene, alkylarylene, alkyl ether or aryl ether moiety having from 1 to 30 carbon atoms; $-(R_5)_qO((CR_3R_4)_rO)_s(R_5)_q$, and $-(R_5)_qCO_2((CR_3R_4)_rO)_sCO(R_5)_q$;

$R_3$ and $R_4$ are independently selected from the group consisting of hydrogen and a linear or branched, substituted or unsubstituted alkyl group having between 1 and 10 carbon atoms;
$R_5$ is independently a linear or branched, lower alkylene or lower alkenylene group;
$R_6$ is independently selected from the group consisting of a linear or branched, substituted or unsubstituted, saturated or unsaturated lower alkyl;
the aromatic ring has from zero to four $Z_1$ substituents, each of which is independently selected from the group consisting of halide, lower alkyl, alkoxy, nitro, alkyl ether, a protected hydroxyl group, a protected amino group and a protected carboxylic acid group;
Y is selected from

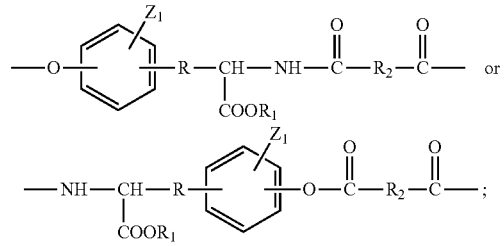

a is 0 to 10;
q is independently 1 to 4;
r is independently 1 to 4; and
s is independently 1 to 5000.

3. The medical device of claim 1, wherein the polyethylene glycol is selected from the group consisting of PEG-3350, PEG-1000, and PEG-400, the polyphenolic polymer comprising about 20% to about 75% of the combined weight.

4. The medical device of claim 1, wherein the at least one drug comprises rifampin and minocycline.

5. The medical device of claim 1, wherein the medical device is comprised of a material selected from the group consisting of a metal, an organic material, a natural or synthetic polymer or copolymer, and a material of biological origin.

6. The medical device of claim 1, wherein a thickness of the coating is 10 μm.

7. The medical device of claim 1, wherein the at least one drug comprises an antimicrobial agent.

8. The medical device of claim 7, wherein at least about 30% to about 50% of the antimicrobial agent, based on the combined weight, is eluted from the coating after about 24 hours.

9. The medical device of claim 7, wherein at least about 80% of the antimicrobial agent is eluted from the coating within about 3 days.

10. The medical device of claim 1, wherein the medical device is an orthopedic fixation device.

11. The medical device of claim 1, wherein the orthopedic fixation device is a screw, tack rod, pin, or plate.

12. The medical device of claim 1, wherein the medical device is a mesh, pouch, or covering.

13. The medical device of claim 1, wherein the medical device is a dressing used in negative pressure wound therapy.

14. The medical device of claim 1, wherein the medical device comprises a material selected from metals, organic natural or synthetic polymers, and materials from a biological origin, wherein the metals include stainless steel and titanium, the organic natural or synthetic polymers include polyethylene, polylactic acid, polyglycolic acid and cellulose, and the material from the biological origin includes porcine heart valves.

15. The medical device of claim 1, wherein the medical device is configured for use for structural reinforcement for muscle flaps, to provide vascular integrity for ligament repair/replacement or for organ support/positioning/repositioning.

16. The medical device of claim 1, wherein the medical device is configured for use in reconstruction procedures involving soft tissue including orthopaedic graft support or stabilization.

17. The medical device of claim 1, wherein the medical device is configured for use in bone fractures.

18. The medical device of claim 1, wherein the medical device comprises a deformable substrate, and the coating is configured to biodegrade such that the coating stiffens or changes a shape of the medical device as the coating biodegrades.

19. The medical device of claim 1, wherein the medical device is selected from a group consisting of implantable access systems, neurostimulators, spinal cord stimulators, breast implants, biopsy devices and patches for delivery of therapeutic agent to intact skin and broken skin.

* * * * *